(12) United States Patent
Yarden et al.

(10) Patent No.: US 10,045,511 B1
(45) Date of Patent: Aug. 14, 2018

(54) CATTLE AND OTHER VETERINARY MONITORING

(71) Applicant: Medisim, LTD., Neve Ilan (IL)

(72) Inventors: Moshe Yarden, Neve Ilan (IL); Ilan Vadai, Hod Hasharon (IL)

(73) Assignee: Medisim, LTD. (IL)

( * ) Notice: Subject to any disclaimer, the term of this patent is extended or adjusted under 35 U.S.C. 154(b) by 0 days.

(21) Appl. No.: 15/232,239

(22) Filed: Aug. 9, 2016

Related U.S. Application Data

(60) Provisional application No. 62/271,747, filed on Dec. 28, 2015, provisional application No. 62/207,490, filed on Aug. 20, 2015.

(51) Int. Cl.
*G08B 23/00* (2006.01)
*A01K 11/00* (2006.01)
(Continued)

(52) U.S. Cl.
CPC .......... *A01K 11/004* (2013.01); *A01K 11/008* (2013.01); *A01K 29/005* (2013.01); *A61B 5/0017* (2013.01); *A61B 5/0059* (2013.01); *A61B 5/01* (2013.01); *A61B 5/11* (2013.01); *A61B 5/742* (2013.01); *A61B 5/7405* (2013.01); *A61B 5/746* (2013.01); *A61B 7/00* (2013.01); *A61D 99/00* (2013.01);
(Continued)

(58) Field of Classification Search
CPC .. A01K 11/004; A01K 29/005; A01K 11/008; A61B 5/01; A61B 5/11; A61B 7/00; A61B 5/742; A61B 5/746; A61B 5/0059; A61B 5/0017; A61B 5/7405; A61B 2503/40; A61B 2562/0223; A61D 99/00; G08B 3/10
See application file for complete search history.

(56) References Cited

U.S. PATENT DOCUMENTS

| 3,070,773 A | 12/1962 | Woolston et al. |
| 3,774,594 A | 11/1973 | Huszar |
(Continued)

FOREIGN PATENT DOCUMENTS

| CN | 102961123 A | 3/2013 |
| CN | 203206907 U | 9/2013 |
(Continued)

*Primary Examiner* — Erin M File
(74) *Attorney, Agent, or Firm* — Lerner, David, Littenberg, Krumholz & Mentlik, LLP

(57) ABSTRACT

Disclosed are a system, device and process for monitoring physical and physiological features of livestock through a unique monitoring system method and device. Basic and Smart tags are placed on livestock to monitor, among other things, temperature, movement, location, posture, pulse rate, and other physical and physiological features. Information is relayed from Basic tags, in one embodiment, to Smart tags that requests the information and receives the information from the basic tags. Smart tags send information to a mobile unit controller and/or home base so that requested information is sent to an end user that monitors the livestock for signs of illness. Potentially ill animals are segregated from the herd for further evaluation and minimization of exposure risk to the rest of the herd. This early detection system saves livestock and ensures a healthier herd for livestock farmers.

21 Claims, 14 Drawing Sheets

(51) Int. Cl.
*A01K 29/00* (2006.01)
*A61B 5/00* (2006.01)
*A61B 5/01* (2006.01)
*A61B 5/11* (2006.01)
*A61B 7/00* (2006.01)
*A61D 99/00* (2006.01)
*G08B 5/36* (2006.01)
*G08B 3/10* (2006.01)

(52) U.S. Cl.
CPC ... *A61B 2503/40* (2013.01); *A61B 2562/0223* (2013.01); *G08B 3/10* (2013.01); *G08B 5/36* (2013.01)

(56) References Cited

U.S. PATENT DOCUMENTS

| | | |
|---|---|---|
| 3,781,837 A | 12/1973 | Anderson et al. |
| 3,972,320 A | 8/1976 | Kalman |
| 4,075,632 A | 2/1978 | Baldwin et al. |
| 4,411,274 A | 10/1983 | Wright |
| 4,471,354 A | 9/1984 | Smith |
| 4,592,000 A | 5/1986 | Ishizaka et al. |
| 4,618,861 A | 10/1986 | Gettens et al. |
| 4,854,328 A | 8/1989 | Pollack |
| 4,865,044 A | 9/1989 | Wallace et al. |
| 4,866,621 A | 9/1989 | Ono |
| 5,203,345 A | 4/1993 | Kennedy et al. |
| 5,818,354 A | 10/1998 | Gentry |
| 6,280,397 B1 | 8/2001 | Yarden et al. |
| 6,292,685 B1 | 9/2001 | Pompei |
| 6,439,768 B1 | 8/2002 | Wu et al. |
| 7,597,668 B2 | 10/2009 | Yarden |
| 2002/0010390 A1 | 1/2002 | Guice et al. |
| 2004/0061606 A1 | 4/2004 | Gronvold |
| 2005/0006452 A1* | 1/2005 | Aupperle ............ A47G 29/1214 232/45 |
| 2005/0065736 A1* | 3/2005 | Bauck ................. C12Q 1/6876 702/20 |
| 2005/0209526 A1 | 9/2005 | Ingley et al. |
| 2007/0107668 A1* | 5/2007 | Eaton ................... A01K 11/008 119/719 |
| 2007/0239038 A1 | 10/2007 | Nicolaescu et al. |
| 2007/0266959 A1* | 11/2007 | Brooks ................ A01K 11/008 119/720 |
| 2008/0204255 A1* | 8/2008 | Flexer .................... A01K 29/00 340/573.7 |
| 2009/0066568 A1 | 3/2009 | Britz et al. |
| 2009/0231138 A1* | 9/2009 | Lai ...................... G06K 19/0707 340/572.4 |
| 2009/0312667 A1 | 12/2009 | Utsunomiya et al. |
| 2010/0198023 A1 | 8/2010 | Yanai et al. |
| 2010/0302011 A1* | 12/2010 | Cervinka ........... H04W 52/0206 340/10.3 |
| 2011/0165286 A1* | 7/2011 | Bachman ................ A01K 5/00 426/2 |
| 2011/0298619 A1 | 12/2011 | O'Hare et al. |
| 2012/0326874 A1 | 12/2012 | Kwak et al. |
| 2013/0222141 A1 | 8/2013 | Rhee et al. |
| 2014/0148196 A1* | 5/2014 | Bassan-Eskenazi .... G01S 11/02 455/456.1 |
| 2014/0345534 A1* | 11/2014 | Rhee .................... A01K 5/0114 119/61.5 |
| 2014/0375431 A1* | 12/2014 | Cristache ............. G01S 13/876 340/10.1 |
| 2015/0282457 A1 | 10/2015 | Yarden |
| 2015/0351369 A1* | 12/2015 | Frazier ................. A01K 29/005 340/573.2 |
| 2016/0066546 A1* | 3/2016 | Borchersen .............. A01K 5/02 382/110 |
| 2016/0135426 A1 | 5/2016 | Harty et al. |
| 2016/0139237 A1* | 5/2016 | Connolly .................. G01S 5/02 340/10.1 |
| 2016/0227738 A1* | 8/2016 | Ausman ................ A01K 5/0233 |
| 2016/0248952 A1* | 8/2016 | O'Neill ................. H04N 5/2254 |
| 2016/0260301 A1* | 9/2016 | Miller ................ G08B 13/2417 |
| 2017/0010920 A1* | 1/2017 | Abouzour ............ G06F 9/5044 |
| 2017/0013802 A1* | 1/2017 | Zimmerman ........ A01K 5/0107 |
| 2017/0156288 A1* | 6/2017 | Singh .................... A01K 11/004 |

FOREIGN PATENT DOCUMENTS

| | | |
|---|---|---|
| WO | 2013082227 A1 | 6/2013 |
| WO | 2014040999 A1 | 3/2014 |

* cited by examiner

Legend:

Cow with "basic" tag

Cow with "smart" tag

Mobile unit portable by vehicle

Fence of feed lot

Farm headquarters with a PC and receiving antenna
arrow indicate the direction of signal transmission

CATTLE AND OTHER VETERINARY MONITORING

The present U.S. Non-Provisional Patent application incorporates by reference the disclosure of U.S. Provisional Patent Application No. 62/207,490 filed Aug. 20, 2015, and U.S. Provisional Patent Application No. 62/271,747 filed Dec. 28, 2015 the disclosures of which are hereby incorporated herein by reference.

FIELD OF INVENTION

The present invention is generally directed to a system, method, and device in the field of diagnostic tools and health monitoring for animals and livestock. More particularly, this invention relates to a system, method, and device in the field of livestock behavior monitoring. This invention relates to a system, method, and device having means for tracking the behavior of livestock, marking an oddly behaving livestock member and identifying said marked oddly behaving livestock member.

Further, this invention relates to a device, method, and system having tags applied to livestock, such tags comprising at least one magnetometer with at least one axis component and/or at least one accelerometer with at least on axis measurement capability, for identifying move-about habits of said livestock, their location, health state or a combination of the aforesaid.

BACKGROUND

Livestock and other animals present well characterized behavioral patterns when they are either healthy or ill. Such behavioral patterns may include, but are not limited to, frequency of arriving at a feeding bunk or station to eat, bringing the animal's head close to the bunks bottom to eat, moving around, standing and lying. Such behavioral patterns, when articulated into an algorithm, may be useful for determining the state of a livestock member by analyzing the behavior and comparing it to an anticipated behavior of a healthy animal or livestock.

One of the most common methods used for raising cattle is through the use of feed lots where cattle is kept in facilities and fattened. When the cattle or other livestock reach a target weight, they are then sent to slaughter.

Cattle, for example, intended for feed lots are bought from a cattle grower and delivered to the feed lot site or alternatively to an on-site feed lot such as a privately owned farm that fattens their own cattle. Upon arrival to these sites, cattle undergo various treatments and procedures, such as: veterinary disease check, castration, weight check and other related health procedures. One of the procedures that are not only part of the farm's routine but is also mandatory by the law in various countries, is the tagging of the animal. Upon arrival at a feed lot, the animal typically is required to receive an ID tag. Such tag is usually connected to the animal's ear and may be linked to that animal's history through its previous ID given at any previous location.

The livestock can be held in feed lots or feed yards whether in a single lot or multiple lots designed for animal feeding operation for a long duration of time. A feed lot may contain varying amounts of animals. Typically 10-100 animals are held per lot. A feed lot's typical dimensions are in the range of 30×30 m to 100×100 m. A feed lot typically contains all the necessary elements for the animal such as water, food and other essentials. The feed lot is routinely accessed by the feed lot staff in order to ensure animal's welfare, health and other needs.

Large feeding operation sites are often comprised of feed lot grids that are a row of feed lots enclosed by fences, in proximity to a service road. Such sites are typically located in far rural areas and usually far off from the farm offices and infrastructures. A single farm can manage several feed lot sites that are separated from one and another other.

A significant part of livestock management is the necessity to monitor and treat the livestock for disease and illness. Both beef cattle and milk cattle are at risk to become infected with one or more of the various diseases occurring in animals.

Cattle like other livestock animals are prone to disease that causes several challenges. The first challenge is economic—ill cattle for example requires additional special treatment, such as human labor for the separation and treatment, special equipment and medicine are also required. In some cases, the disease will end in the animal's death—causing more economical loss. A second challenge caused by animal illness is the risk for zoonotic diseases or namely diseases that can be transmitted from animal to humans. Such diseases might lead not only to economic damage, but also lead to a hazard to human health.

Different diseases are caused by bacteria, virus or other agents. Cattle disease influences different systems in the organism such as the respiratory, digestive, reproductive, neurological or other systems and can be expressed by a large variety of symptoms. Such symptoms can include, but not limited to: coughing, nasal and eye discharge, salivation, depression, lack of appetite and dullness, as well as other symptoms. In addition, one of the more significant symptoms leading to a diagnosis of disease is animal's high fever.

As the disease goes undiagnosed and untreated, it causes greater damage to tissues and organs which might eventually become permanently damaged. If identified early enough, the disease may be treatable by various means, such as medications or other methods. An early identification of an ill herd member will allow an early onset of treatment, and thus may:

1. Lower the chances of contamination to other members in the herd
2. Lead to less complications and tissue damage
3. Lead to less chances for future disease relapses
4. Lower the mortality rate One of the techniques currently and commonly used for the identification of sick cattle is a visual method. The farm staff visually examines the livestock to check for any changes in the animal's appearance or behavior. While such a visual method is based on the logic that a sick animal should express different behavior or illness symptoms, it has several significant drawbacks.

The visual scanning solution lacks an objective and clear parameter for illness identification. The subjective visual check might be false-negative, namely—the person scanning the living stock might miss a sick animal due to lack of experience in identifying the characteristic signs and symptoms, cattle attempt to hide or mask signs of disease, or other reasons. On the other hand, a false-positive event of disease identification might also occur. Such case might lead to a waste of different resources and unnecessary medication treatment to the animal. Also, visual identifiable symptoms might occur relatively late in the disease course beyond the point of recovery for the animal.

Therefore, there is a need for a system capable for early detection of sick cattle and efficient transmission of the information to the farm staff.

Feed lots, often are located in rural areas with minimal technical infrastructure for maintenance or support. The cost of any monitoring system must be considered, as cost sensitivity in this industry is very high. The environmental conditions such a system needs to withstand are very tough. Environmental conditions, include, but are not limited to, extreme high and low temperature, dust, humidity, mud and dirt. Therefore any solution must address at least these needs.

Furthermore, farmers typically observe movement and habits of livestock in a breading pen (feedlot for example), as well as frequency of eating, but not only, to gain knowledge of the health of livestock. Knowledge of movement, patterns, frequency, and preferably physical location within a breading pen is difficult for farmers when large herds are concerned since it is difficult to segregate the unhealthy animal from the large herd. There is a need that will allow to identify whether a livestock member is moving-about less or differently than normally anticipated, and whether said livestock member arrives at either the feeding bunk or a drinking bunk (or both), in a frequency lesser then the anticipated from a healthy livestock. There is also a need to identify when a livestock animal has lesser eating and\or drinking in order for a farmer to indicate an abnormal health state of the livestock animal. It is advantageous to be able to provide such indication to the farmer attending the livestock.

SUMMARY OF THE INVENTION

The current invention is an effective system, method and device for early and objective identification of cattle or other livestock suspected of being ill, by using data sampled from the animal and related to its health and/or wellbeing. The technique to achieve this target entails monitoring of different signs or symptoms which are characteristic to ill cattle, such as high fever and lack of appetite, movement decrease or other types of behavior.

These signs and symptoms are monitored by a dedicated system (CMS—cattle monitoring system), that measures the relevant data, process it and transmits it, together with the ID of the relevant cattle or animal to the farm staff in charge of the animal's welfare. In an embodiment of the present invention, to overcome multiple livestock tags' data being transmitted at same time causing for loss of data, the tags are preprogrammed so that their transmissions are time elapsed. In another embodiment of said invention, the data is transmitted within several different, spaced apart radio or acoustic frequencies.

Provided with such information, the farm staff will be able to take different actions in order to verify the animal's health state and if necessary—withdraw the animal from the herd or feed lot for a more thorough examination. Thus, a fast and efficient treatment is assured. In another embodiment of the present invention, based on data received from the Tag concerning a livestock member's behavior (thus eating patterns), the system affects: (a) a discouraging signal to said livestock member, intended to discourage from or to encourage that livestock member to approached the bunk and eat. In another embodiment of the present invention, said data is used as an input to the feedlot management software to recommend altered handling of said livestock member, for example moving to another feedlot, or apply an alternate diet to increase or decrease said member's weight.

The system is designed to be implemented at very low cost, with minimal or no infrastructure requirements in the feed lot itself. The Cattle Monitoring System (also referred herein as CMS) consists of several key components. These components, include, but are not limited to, a Basic tag (also denoted herein as BT), Smart tag (also denoted herein as ST), Mobile unit (also denoted herein as MU) and PC unit.

The present invention further discloses a device and method for gathering and providing such information, using a livestock worn tag, said tag comprising a magnetometer component and/or accelerometer sensor.

The present invention utilizes a combination of at least two one of the following steps: (a) receiving signals from sensors (b) identification of an abnormal health state of a livestock using a logic applied to determine such a state is in effect, (c) notification that a certain livestock is in such a state, whereas an external hardware becomes informed a certain livestock member, and (d) distinguishing from the rest of the herd, i.e. allowing for identifying that a certain livestock member in an abnormal state of health, by creating a notable alert.

In the present invention, the Identification of an abnormal health state of a livestock may be done using a sensor or sensors which their output may be used separately or in combination with one another or in combination with previous patents. Such sensors may provide information useful for determining the livestock's: movement, chewing patterns, proximity to a feeding area, location within the pen or feeding area (bunk), location determined by being actuated by another piece of hardware or by a physical proximity to another piece of hardware located at the bunk or drinking area.

In the present invention, the determining of an abnormal health state of a livestock member may be done by applying a logical principal for a logical deduction, based on information gathered by one or more sensors.

In the present invention, the notification of an abnormal health state of a livestock member may be communicated in any of several ways, or a combination thereof: a livestock tag providing a signal indicating health or abnormal state of a specific cattle, ID and/or relevant data communicated to the feeding area indicating every cattle which is eating, data communicated (or not communicated) to another stationary or mobile communication device.

Magnetometers, are measurement instruments used for two general purposes: to measure the magnetization of a ferro-magnetic material like iron, or to measure the strength and, in some cases, the direction of the magnetic field at a point in space on earth.

A livestock breading pen typically comprises a feeding bunk, or an area along a service path used as a feeding bunk along one of the pen's fence, where the food for the livestock is disposed. The pen is typically circumferential with a metal fence or metal bars, and the bunk or service path is separated from the pen by such metal bars or fence. Typically, there are no other metal objects or bars within the pen, other than the fence bars.

In one embodiment of the present invention, the magnetometer, identifies a repeated proximity to a metal object along the day, thus one can concluded the livestock has attended the feeding bunk or feeding. Collecting data of such repeated visits to said feeding area with or without the time pattern of such visits, or the absence of visits after a period of daily repeated visits, may be used as indicating information to a livestock not attending the feeding area, and possibly being unhealthy.

In another embodiment or in a combination with the previous proximity indication of the present invention, the magnetometer provides data teaching of the livestock moving about in a certain direction, several times each day, indicating attending the feeding area. The lack of such movement, in said directions, preferably but not necessarily in conjunction with information from other sensors, may be indicative of the livestock's possibly being unhealthy or abnormally eating. In an embodiment of the present invention, the directional location of the feeding area with respect to the magnetic North is determined and stored in a memory component the tag for reference. In addition to said magnetometer component, a tag used to monitor a livestock member may include, but not limited to at least one of the following components: a clock component, a memory component, a transmitter component, a receiver component, a processor, a controller, a power source, and audio component, an accelerometer, tilt sensors, light sensors or temperature sensors. By way of example, using accelerometers and/or tilt sensor may be useful for identification of move about patterns of the livestock along the day, but also for identification of the jaws movement indicative of eating.

The tilt sensors may indicate the head's disposition for reaching the food in the feeding bunk. Thus, the accumulation of such data from such sensors, is useful for determining behavior patterns different than normally anticipated. Preferably, but not necessarily, combining such information from one or more said sensors, with the information available for the magnetometer, is useful for identifying an abnormally behaving livestock, thus indicative of a change in its well-being.

The combination of the magnetometer and the accelerometer can be used to determine the location of the cattle. By integrating twice the accelerometer output, one can get the velocity and distance travel of a cattle. Knowing the direction of such a movement which can be derived from the magnetometer sensor one can determine the location of the cattle within the feedlot.

A less accurate, but still useful and cost effective, is a combination of a tilt sensor and magnetometer. The tilt sensor output can provide indication of cattle steps as a pedometer. Combining this data with the direction data (azimuth angle) received from the magnetometer output processing, will provide a good estimation of the cattle location.

Once every period of time the system may reset the location based on indication of presence near the bunk as explained above, thus a more accurate location may be calculated.

Another combination of sensors may be a Magnometer an Accelerometer and\or a tilt sensor or sensors, wherein the disposition of the livestock member may be correlated these sensor's data. In addition, filtration of non-relevant movement's indication may be useful for determining which accelerometer movements are attributed to eating, or to disposition with n the pen and which ones are random meaningless.

The data from the sensors may be stored, analyzed, transmitted, indicated, or any combination thereof, to provide the livestock tending person with valuable information concerning the livestock's wellbeing.

The data from the tag or tags, may be received in a unit affixed in the feeding area, such as a feeding bunk, configured to receive a data transition from a tag, to transmit data transition to a tag, or any combination thereof, thereby allowing the livestock tending person to become aware of abnormal movement or otherwise monitored habit of the livestock.

In another embodiment tags are placed on a livestock, to identify, track and possibly record information indicative of livestock member's movements or location. Such tags may transmit said information, or may receive information from another device. The tag may also comprise means creating notable alerts indicating a certain livestock member among the herd.

The tags may send information to either a stationary or a mobile unit, directly or indirectly, which in turn may send information or a processed output of such information, to a herd operator that monitors the livestock over for health and/or feeding state. This early detection system allows for improved herd health management for farmers.

In one embodiment, using such tags comprising magnetometer components and a method using information derived from such tags, preferably but not necessarily in conjunction with other sensors, is believed to be advantageous to prior art in the field.

The information derived from said magnetometer comprising tag, may be transmitted to a management system, such as a herd management software, to provide a herd operator with information concerning the well-being of an individual livestock member.

The principal of using a combination of data from sensors, and cross correlating their data, preferably but not necessarily using a logic, is a useful way to provide for both (a) Identification of an abnormal health state so the "livestock will know" and provide an alert, and (b) Communication said abnormal health state so another piece of hardware, like a feeding bunk based transceiver that becomes informed that a certain livestock member is not well.

Another use of the magnetometer in this respect may be to determine proximity to a feeding bunk, by identification of proximity to a metal element, like a bar, which if tracked to occur several times per day, in daytime, may indicate visits to the feeding bunk.

The foregoing features are achieved and other features and advantages of the present invention will become more apparent in light of the following detailed description of exemplary embodiments thereof, as illustrated in the accompanying drawings.

BRIEF DESCRIPTION OF THE DRAWINGS

In the drawings, wherein similar reference characters denote similar elements throughout the several views.

DETAILED DESCRIPTION

Figure 1:
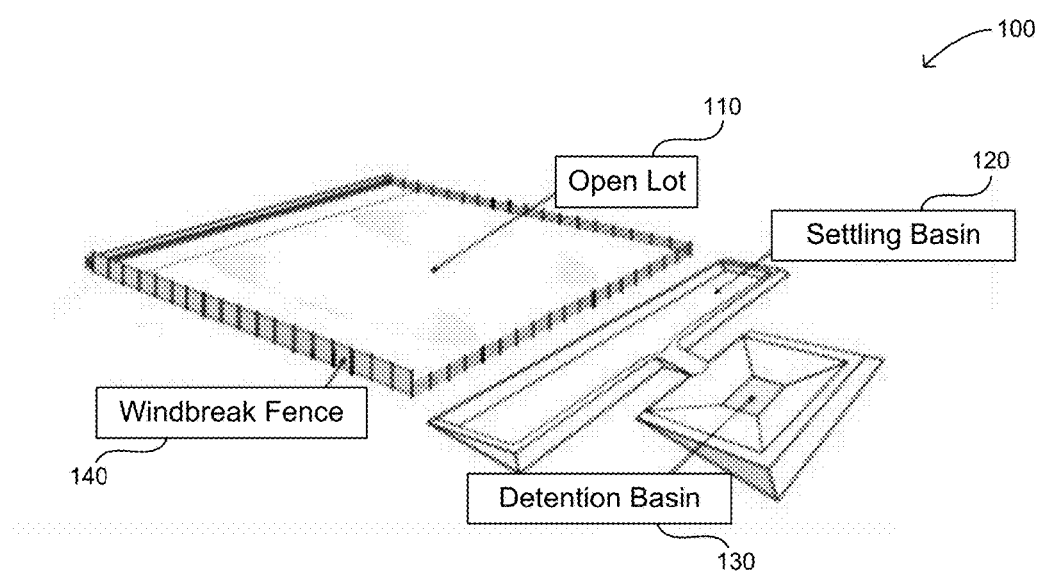
FIG. 1 shows an illustration of an open feed lot structure.

The present invention comprises, among other things, several steps, preferably but not necessarily used all in conjunction:

a. Obtaining a Livestock Tag—the tag comprising a sensor or combination of any of the following sensors out of a list comprising, but not limited to: a temperature sensor movement\acceleration sensor, light sensor and sound sensor, said sensors enclosed in a tag attached to the livestock, preferably but not necessarily to the earlobe. The sensor\s sampling data is stored, and processed in an IC. The tag may, depending on the embodiment, also comprise at least one acoustic transmitter component (such as a speaker), one acoustic receiver component (such as a microphone), one light emitting diode (LED), such light may be of a different wave lengths, one photo diode ("light sensor") or any combination thereof.

b. Obtaining a Bunk Transceiver—a bunk mounted device comprising at least one acoustic transmitter component (such as a speaker), one acoustic receiver component (such as a microphone), one light emitting diode (LED), one photo diode ("light sensor") or any combination thereof. Said receiver and transmitter components are used for data exchange with the Livestock Tag. The Bunk Transceiver may also comprise a radio transceiver component (RF, Wi-Fi, Bluetooth etc.) for transmitting data. The Bunk Transceiver may also comprise a RF transmitter and antenna for actuating signal for the tag. It is noted that more than one Bunk transceiver might be installed per pen depending on the embodiment.

c. Actuating Tag's transmitting. In one embodiment of the present invention, a Remote Actuator is used to activate the Livestock Tag transmitter circuitry when said tag is present in a predefined proximity to the bunk. The purpose of such actuator is to allow for the tag to be in an energy saving mode until actuated by the actuator. Such actuator can be based on a radio frequency (RF) method, acoustic method or light emitting method. Such an actuator is designed to have a limited range to avoid false actuating of Tags which are remote from the bunk (for example, not eating). Yet in another embodiment of the invention, the Livestock is actuated regardless of an external actuator.

d. Transmitting data from the Tag to the Bunk Transmitter, and\or transmitting from the Bunk Transmitter to the Tag.

e. Logging data in the Livestock Tag, the Bunk Transceiver, or both. In one example, data may be indicative of the appearance or non-appearance of a livestock at the bunk like its moving about the lot, the time of such moving about, and other such related movements.

f. Forwarding said data to a remote device, either a stationary or mobile computing device. Such a mobile device might be installed in the feed truck and communication may take place while a feed truck is dispensing the food to the bunk.

The present invention suggests improvements to alternate presently available solutions, and is disclosed herein. Below are some examples.

Transmitting data, from a livestock Transmitter Tag, sets challenges concerning the efficacy energy consumption for the needed transmitting. An efficient and economically viable transmitting Tag mounted on a livestock, is preferably disposable after being operational for a months periods. Such a tag, if using RF based transmittance, requires an electrical power source to be able to provide for months of said transmitting.

The present invention provides advantageous alternatives to RF transmitting by using at least one of the following steps for providing needed data for determining odd behavior of a livestock member. Such data may include movement patterns and frequency of arriving at the Bunk and eating. The following elements are preferably but not necessarily used in combination:

a) A livestock worn transmitter Tag for transmitting data, receiving data, or both, by way of acoustic signals transmitted from said Tag comprising at least an acoustic transmitter, such as a piezoelectric speaker. Said data may be also transmitted (or received) using infrared transmission, adjunct or surrogate to the acoustic transmission.

b) A Bunk transmitter for transmitting data, receiving data, or both, by way of acoustic signals transmitted from a Bunk mounted unit comprising at least an acoustic transmitter, such as a piezoelectric speaker. Said data may be also transmitted (or received, but not necessarily, using infrared transmission, adjunct or surrogate to the acoustic transmission.

c) Bunk data Logger component within the Bunk transceiver, for elective downloading or to transmitting to another unit, of data received from the livestock's Tags.

When a livestock is determined to be oddly behaving (sick, fever, not eating etc), the tag attached to such livestock is providing a notable indication signal to enable the signaling or locating of said livestock for further treatment.

In such case, in one embodiment of the present invention, the livestock worn Tag, is providing a notable indication. Such notable indication may be, but not necessarily, related to an oddly behavior of the livestock member wearing it. Such notable indication may relate to information concerning said livestock member. The notable indication may be provided by an acoustic signal using a speaker or otherwise acoustic transmitting device, and\or a visual signal using a LED or other light emitting component, or an RF data transmission.

As the said oddly behaving livestock which its tag creating such notable indication, may not be easily identifiable by a person looking to identify the said livestock wearing said Tag, an identification aid device (to identify or cingulate said notable indication) is disclosed. Such an aid device may be, by way of example:

a) In the case of acoustic signal, the aid device may be a shotgun microphone (or other type of microphone) or a directional microphone to identify direction of the Tag and thus the oddly behaving, marked, livestock.

b) In the case of visual signal, the aid device may be a vision apparatus having polarized lenses, which will provide for outstanding of the LED emitted light signal.

The invention will now be described in detail with reference to the accompanying drawings. The present invention relates to a system and method and device for monitoring and tracking the wellbeing, health, and activity of livestock either remotely, mobile, or at a stationary post.

Shown in FIG. 1 is an illustration of a typical open feed lot structure 100. Lot 100 has an open lot 110 surrounded by windbreak fence 140. The fence secures the livestock in open lot 110. Also shown is a settling basin 120 connect to a detention basin 130. The detention basin 130 is typically where livestock that is sick or shows signs or symptoms of being ill are kept for further observation and evaluation. The detention basin 130 also serves to separate the livestock from the other livestock animals so as to minimize any outbreak of illness or spread of any contagious illness. Early detection of any illness is important to minimize the spread of any illness to the rest of the livestock.

Figure 2:
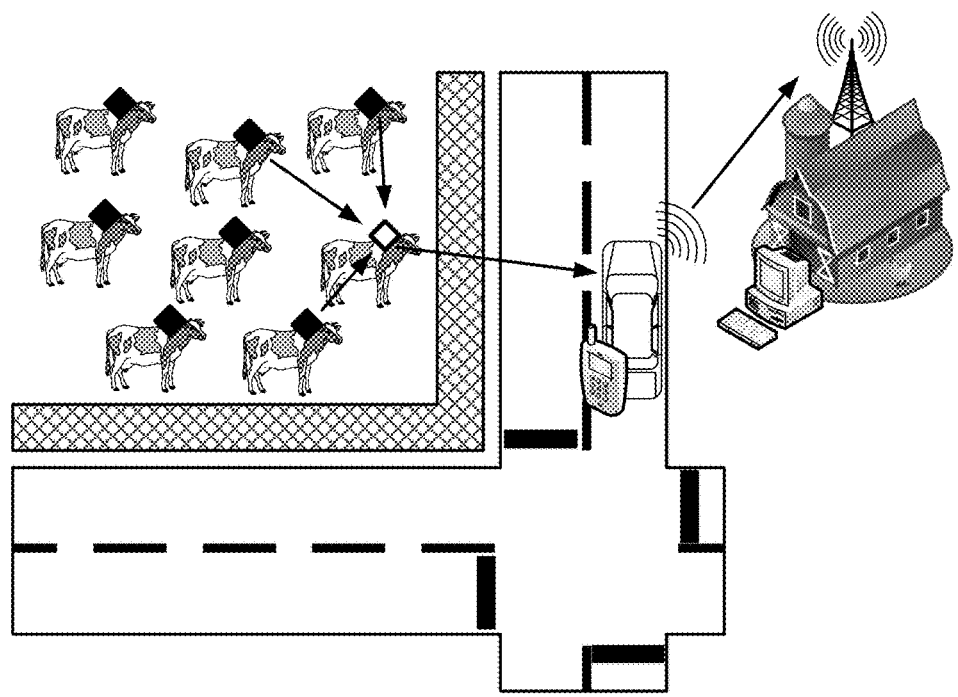
FIG. 2 shows one embodiment of a general overview of a system and method for sampling livestock information and transmitting the information to mobile and/or stationary units.
Figure 2:
Figure 2:
Figure 2:
Figure 2:
Figure 2:

FIG. 2 illustrates a description of various information collected from livestock through a Smart Tag (or Relay Tag) and a Basic Tag. Shown in FIG. 2 are cows with Smart Tags and Basic Tags in an open lot. A mobile unit portable by a vehicle or other eMobile means can monitor several cows. Alternatively or in concert with, a stationary base wither in a farm or other structure may act as the headquarters with a personal computer or other device and a receiving antenna to receive signals from the tags. The communication flow can be from the tags to the mobile unit to the stationary headquarters or to the mobile unit and/or stationary headquarters directly, depending on the implementation of the invention.

Figure 3:
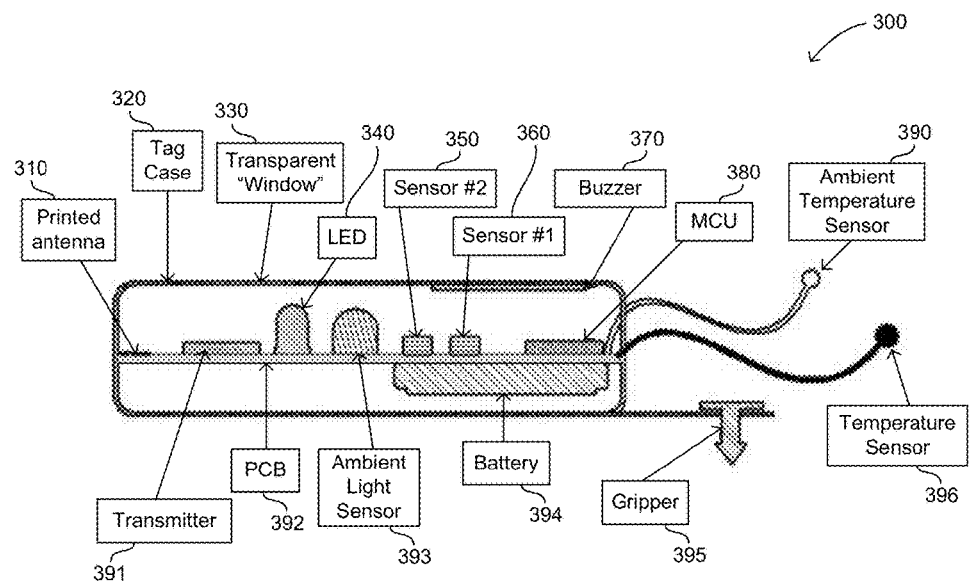
FIG. 3 shows a schematic diagram of one embodiment of a tag structure shown in FIG. 2.

FIG. 3 shows a side view of the insides of a basic tag structure. The basic tag 300, or BT, is used for the measurement and transmission of information relevant to the animal's health and well-being. For that purpose it comprises a temperature sensor 396 and/or at least one more sensors; sensor 350, sensor 360, used to measure parameters of motion, feeding, behavior, temperature, or other features, as detailed herein. Sensor 390 is used to measure ambient temperature.

Figure 4:
FIG. 4 shows an illustration of a livestock animal with the tag in FIG. 3.

The data obtained from the different sensors sensor 350, sensor 360, sensor 390 and sensor 396 together with the animal's ID number is then transmitted to the Smart Tag 410 or ST 410 on animal 400 in FIG. 4, operating as a relay station between the basic tag units 300 and the mobile unit, which collects the data from all of the animals being tagged. The smart tag also performs all the basic tag functions. Thus, the cattle which carry the Smart Tag can also be monitored as the cows with the basic tag.

In one embodiment, the ST processes the data received from the BT in order to provide an evaluation of the health status and other status or conclusions regarding cattle's status. Yet, in another embodiment, data is analyzed by the BT unit and the transmission to the ST unit includes only indication on the cattle status which carries the BT together with the relevant ID number.

As shown in FIG. 2, the mobile unit is only temporarily present in the area of every feed lot (mobile by car or manually), and thus it is used for an occasional and periodic data collection from the tags. The collected data is further transferred to the PC unit, used to process and store it for the system use.

The PC unit may transfer different necessary information to the mobile unit, such as future transmission timings, instructions for feed lot worker or others.

In order to implement the Cattle Monitoring System or CMS in a feed lot, it is necessary to execute an enlistment procedure, comprised of two main steps:
1. Attaching a tag (simple/basic tag or smart tag) to every cattle unit. The tag may be attached to the cattle's ear or other suitable location.
2. Creating a database of all the tags.
    The database may be carried on:
    a. Smart tags (containing all the simple tags in their reception range), and/or—
    b. MU, that may contain a database of all the STs in the system, and/or all the BTs related to every ST.
    c. PC, containing a database of all the STs in a particular feed lot and all BTs related to a certain ST. In case of a farm that contains more than a single feed lot location and/or more than a single MU, the PC may contain also a database of MUs related to a specific feed lot area.

The implementation of the tags into the system's database may be done by recording every new active tag in the area of the mobile unit or MU into the database, and distributing it according to the required specifications:
Basic or smart tag
If basic tag—what smart tag it is related to
data recorded in the MU is then downloaded or transmitted to the system PC.

The basic tag as seen in FIG. 3 is the fundamental unit of the system, containing the necessary components for cattle monitoring and data transmission. Basic tag 300 components include, but are not limited to, temperature sensor 396, Transmitter 391, microcontroller unit (MCU) 380, and Memory (ID and data storing) that may also be in the MCU 380.

Optionally, the basic tag 300 may also contain:
Transceiver or transmitter 391, Led light emitting diodes 340,
Buzzer 370, Ambient temperature sensor 390, Ambient light sensor 393, Motion sensor or Sensor (#1) 360 (in a form of: Piezo electric/piezo resistive sensor, accelerometer, tilt sensor, GPS, or possibly a combination between at least two of these sensors), Proximity sensor or Sensor (#2) 350 (in a form of a capacitive, inductive, magnetic, photoelectric, ultrasound, RF or other type of proximity sensor, or possibly a combination between at least two of these sensors) and Battery 394.

The BT or ST tag is comprised from the tag case 320, the electrical components such as a printed circuit board (PCB) 392 and a gripper 395 that is used to attach to the animal subject.

Depending on the embodiment the means for attaching the tag to the livestock animal may include, but is not limited to, a mechanical gripper, piercing device that pierces the skin of the livestock, chemical or adhesive used to stick to the livestock either permanently or temporarily, or magnetic device to hold the tag on a metal piece attached to the livestock and any combination thereof.

The case is designed to protect the components from the feed lot environment, and the dimensions of it allow placing it on an animal. A printed antenna 310 may also be used in the tag. A transparent window 330 is used to see warning lights such as LED 340 and/or Ambient light sensor 393. Custodians of the livestock may also hear warning of a potentially ill livestock through sounds made in buzzer 370.

In one embodiment of the present invention, the Tag attached to a livestock's outer surface, preferably but not necessarily to its ear, further includes one, or more than one, surface temperature sensor or sensors, configured to be applied to said external surface of the livestock.

The core temperature of the livestock is then calculated by correcting for a difference between the livestock core's temperature and the measured surface temperature. Examples of the function used in the core temperature determination include, but are not limited to, those found in the disclosure of U.S. Pat. No. 7,597,668, that is incorporated by reference in its entirety herein.

The components shown in FIG. 3 may also be utilized for both a BT and/or ST tag and perform the tag's different functions: data storing and measurement, optionally—data processing and data transmission, as detailed herein.

Optionally, sensor #1 may be a motion sensor and sensor #2 may be a proximity sensor, or both sensors may be of the same kind (proximity or motion). Optionally, the tag may include more than two sensors.

The gripper 395 is intended to connect the tag to the animal. The tag 300 may include a printed or recessed ID number that corresponds to the ID stored in the BT memory.

Basic Tag Functionality

The basic tag 300 might be placed on the cattle's body (ear, neck, tail or any other body part). The basic tag's main functionalities are:

Cattle ID
Cattle illness-related data measurement
Optionally—data processing
Data transmission
Alarm display to farm staff
Cattle ID Every tag includes a specific and unique identification number burned into the tag memory or MCU. The ID number might also be stamped on the external side of the tag, visual to the farm staff. The tag's ID is transmitted to the ST in conjunction with the other information regarding the specific cattle, such as cattle status and/or measured temperature and movements (as specified and detailed herein).

During the reception and enlisting process, every tag ID is attributed to specific cattle, allowing its history and particular feed lot tracking, and/or the particular ST it should transmit to.

The full list of BTs, also as information regarding to which ST every BT is related (based on ID received for the specific cattle upon arrival), is saved in the system database as detailed herein.

Cattle-Illness-Related Data Measurement Functionality
Temperature Measurement.

The basic tag contains a temperature sensor 396 (in a form of a thermistor or, optionally, another type of sensor) measuring the animal's temperature. The measurement might be performed continuously with a predetermined duty cycle, during all day and night, in order to allow a prompt tracking of temperature alterations. In some embodiments the duty cycle of temperature measurement may be adaptive, according to the battery status and/or environment conditions in order to save battery life.

The information gathered is then analyzed and transmitted in its raw form to a Smart Tag (ST Unit), in conjunction with the specific cattle ID, at every pre-determined period of time, using RF communication, microwave transmission or the like. In another embodiment, only the cattle ID and the outcome of the sampled data analysis in form of cattle's status is transmitted to the ST unit.

Physical/Physiological Parameters Measurement

The tags are measurement devices of Physical/physiological parameters and measurements, such as, but not limited to, mobility, eating or other types of behavior measurement, such as tail and ears movement, breathing, trembling, pulse rate, or shivering in addition to measurement of temperature of the livestock.

The basic tag optionally includes additional sensor (or several sensors) for the purpose of which is measuring signs, behavior or symptoms that may provide information relevant to the cattle's health or illness state. These symptoms may be related to the cattle's mobility patterns. Illness in the livestock might cause weakness, resulting in slower movements, or a decrease in movement amounts of sick cattle for example. For that purpose, it is possible to use different kinds of sensors. Suitable sensors may be, but not limited to:

An accelerometer—measure amount of movements, speed of movement, mobility pattern, tail movement. It is possible to install more than one accelerometer so two or three axis measurements may be made. All accelerometers can be mounted perpendicular to each other.

Tilt sensor—may measure head movement and position, tail movement or possibly the rumination. It is possible to install more than one sensor so two or three axis measurements can be executed. All sensors can be mounted perpendicular to each other.

Piezo electric/piezo resistive sensor—for the measurement of tremor, shake, rumination or general movement count.

Proximity sensor, in a form of a capacitive, inductive, magnetic, photoelectric, ultrasound, RF or other type of proximity sensor—in order to measure proximity of cow to other herd members, proximity of cow to feeding pan, water tank, fence of feed lot or other options.

GPS—in order to monitor for a change in locomotion pattern (moves less, moves slower, moves to different sites of feed lot than usual), proximity to feeding pan, watering tank, fence or other).

Ambient Data Measurement

The basic tag (BT) may also provide information about the conditions in the cattle's environment, in terms of temperature and light, by measuring data from the following sensors:

Ambient temperature sensor—providing information about the environmental temperature proximal to the cattle's body. Such information may be relevant for cattle's body temperature calculation, as described hereunder.

Ambient light sensor detecting ambient daylight time—Information from this sensor may be cross-checked with other data such as movement or any other measured parameter, in order to aid the decision making process. Such a decision may be related to the normality of behavior or measured parameter pattern (for an example—an animal that is detected to be still for a long period may be considered to behave normally if it is night time, but not if it is day time). Information about daylight time might also be derived from the ambient temperature sensor by using the difference in ambient temperature between day and night time.

Data Processing Functionality

Optionally, the basic tag may process the data received from the different sensors on the tag. The data processing may be performed on the tag's MCU component and may include the next parameters/endpoints:

Cattle Temperature Calculation.

An algorithm used inside the MCU may be based on data received from the temperature sensor and/or ambient temperature sensor in order to eliminate the influence of the surrounding temperature on the temperature sensor and/or on the temperature of the cattle body itself. In this form, the calculation result is the cattle's body temperature.

Cattle Temperature State (High, Low, Normal).

The algorithm is using information received from temperature sensor combined with information from the ambient temperature sensor and/or additional sensors such as the ambient light sensor and/or other sensors used to measure physical/physiological parameters such as mobility, eating or other types of behavior measurement in order to calculate cattle's temperature state—normal, lower than normal, or higher than normal.

The information from the additional sensors is necessary in order to provide a decision about the normality of the cattle's temperature.

For an example—cattle's body temperature may vary by time of day. The input from the ambient light sensor may provide the algorithm with the estimated time of the day (morning, noon, evening, night) so the decision about the temperature's value normality may be made according to the expected normal temperature range for this particular time of the day.

Another example—cattle's body temperature may vary as a result of hormonal changes, for example when a cow is 'in heat'.

Information indicating a hormonal change may be received from the different kinds of motion sensors as described herein. Hence, a cow in such a state is expected to be restless and thus move more.

Cattle Physical Sign/Physiological Parameter Normality

Depending on the implementation, the algorithm may use information received from one or more of the sensors of the BT: the ambient temperature sensor and/or additional sensors such as the ambient light sensor and/or other sensors used to measure physical/physiological parameters such as mobility, eating or other types of behavior measurement—in order to calculate cattle's normality of physical/physiological parameters.

As an example, the algorithm uses data from the motion sensor in order to calculate amount of movements made by the cattle, in order to determine regarding its normality.

An additional and detailed description of cattle's possible signs and symptoms of illness are found herein: "Possible signs and symptoms monitoring, using different kinds of motion sensor".

Optionally, a part of the data processing functionality may be an algorithm that cross-correlates outputs of different sensors to provide a decision about cattle potentially being in an alarm-requiring state.

Battery State

Battery state is monitored and compared to the predetermined threshold of voltage, below which the battery is considered low.

Data Transmission Functionality

Data acquired and/or calculated by the BT is transmitted to the ST along with the cattle ID. Data to be transmitted may be stored on the MCU's memory, or on an external device memory. The transmission may be executed via an RF, by implementing the transmitter located on the BT. Transmission-related different parameters such as: transmission encoding, protocol, rate and other parameters may be predefined for the CMS.

Alarm State Display to Farm Staff Functionality

The alarm display functionality is activated according to the results obtained by the data processing functionality of the tag. In case there is a need to signal an alarm (abnormal temperature and/or abnormal behavior and/or abnormal physical or physiological parameters measured, and/or low battery), the tag signals an alarm by at least one of the following components:

Activating a LED that helps visually identifying a sick animal in the lot or herd.

Activating a buzzer that aids for audio-identification of a sick animal in the lot or herd.

Figure 5:
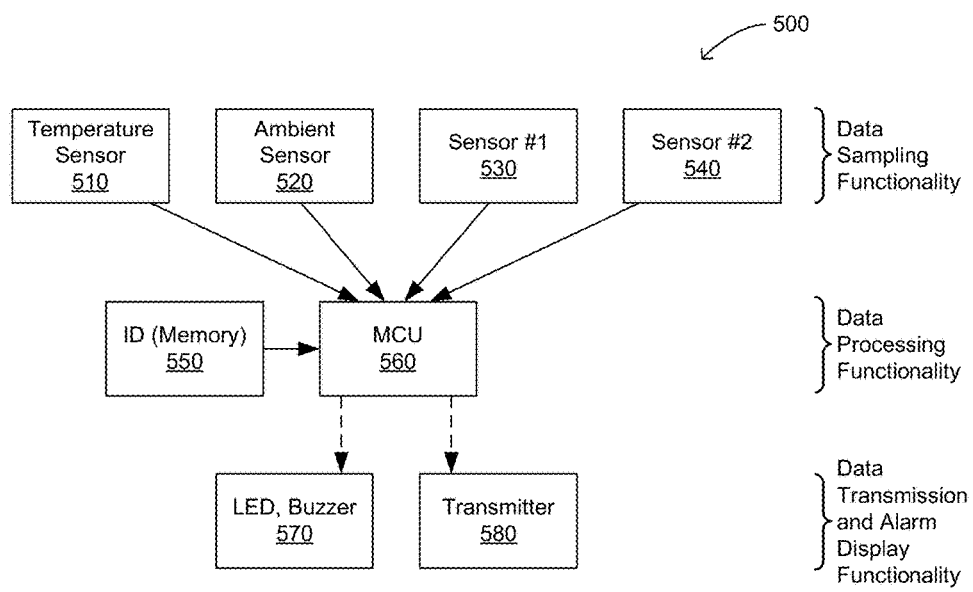
FIG. 5 shows a block diagram related to basic tag functions for the tag in FIG. 3.

FIG. 5 demonstrates the relations between different functionalities of the CMS in use of the basic tag BT 500. Data measured by sensor 510, sensor 520, sensor 530, and sensor 540 is transferred to MCU 560. Sensor #1 530 and #2 540 may be ambient light sensor, ambient temperature sensor, motion or proximity sensors as detailed in herein. Data processed in the MCU 560 as well as the ID of the livestock that is stored in ID memory 550 is forwarded (dashed arrows) to the transmitter 580. The processed information is also forwarded to the alarm-display components 570, activating them if necessary.

Smart Tag

Figure 6:
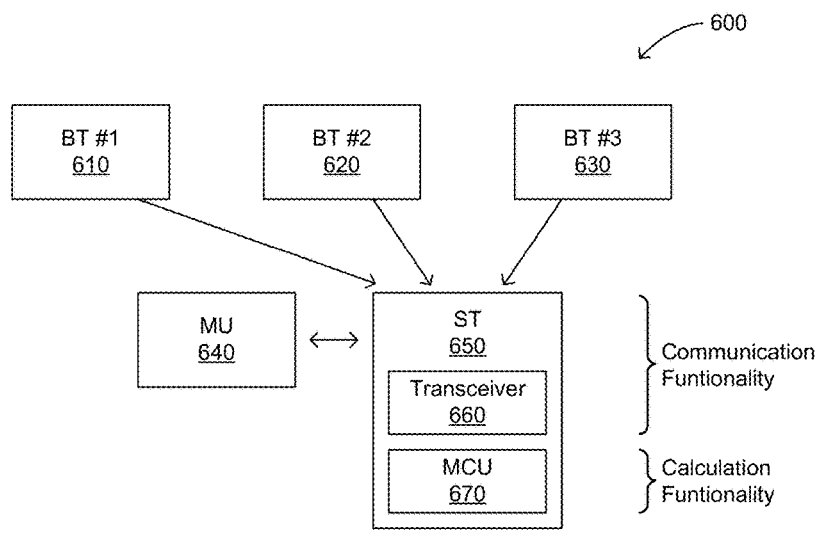
FIG. 6 shows a block diagram related to smart tag functions for the tag in FIG. 2.

FIG. 6 illustrates the Smart Tag (ST) 600 functionalities, and in particular are highlighted features that are not included in the BT. It is within the scope of the invention for ST to include in addition to its special features all the functions as well of the basic tag (BT). The data obtained from the different sensors, or the analysis output indicating the cattle status is transmitted from all BTs 610, 620, and 630 to the ST 650 as shown in FIG. 6.

The ST 650 is operating as a relay station between the basic tag units and the mobile unit 640, which collects the data from all of the animals being tagged. The smart tag performs all the basic tag functions as described herein and thus, the cattle which carries the smart tag can also be monitored. A transceiver 660 receives signals from the BTs. A MCU 670 within the Smart Tag computes the information from the BTs and from the livestock it is on, if applicable, and send the information onto the mobile unit MU 640.

Smart Tag Components

The ST components are identical to the BT components as listed herein, with exception to the transmitter, which is replaced in the ST by a transceiver 660. This enables the ST to send and receive signals, instead of just sending signals like the BT.

Smart Tag Structure

The ST structure is identical to the one of the BT described in FIG. 3, with the transmitter component replaced by a transceiver component 660.

Smart Tag Functionalities

The smart tag includes all the functionalities of the basic tag, as detailed in this specification. It also contains additional data processing functionalities and transmission functionalities as detailed hereunder. It may have the same form of the basic tag, or a different structure. It is also possible for the CMS not to include smart tags (in such case the system will include basic tags, mobile unit and a PC.

ST Functionalities (Additional to BT):
1. Data processing functionalities
2. Communication functionalities Data processing functionalities—Calculation of time elapsed.

Such a calculation may be performed regarding last data transmission from of a particular BT to ST, or data transmission by ST to MU. This calculation may be performed by using an inner timer in the ST and BT.

The time elapsed is required in order to monitor for a lost signal or potentially a tag with a low battery, both of which may be suspected in case time elapsed from last data transmission (BT to ST) is longer than the predetermined period. As to data transmission from ST to MU—amount of time elapsed may be the method to set the next rendezvous between MU and ST. It is required in order to save the ST battery life, by reducing the time it stays in reception mode and limiting it to the rendezvous window.

Generation of Potentially Alarmed Tags List.

The ST may generate a list of all BT's ID in the feed lot that has transmitted an alarmed state (or sensor-measured information from the BT that was processed on the ST and was found to meet alarm criteria).

Communication Functionalities

All kinds of data transmission performed by the ST are executed by the transceiver component of the ST.

Data Reception from Basic Tag

The smart tag 600 allows data collection from several "basic" tags 610, 620, 630. The data is received via a transceiver 660 and is temporary stored in the ST's memory component and/or MCU component 670, in order to be later transferred to the MU 640 by means of RF communication, microwave signals or other communication signals.

Data Transmission to MU

One or more ST transmits to the MU a list of all the BT's IDs that are potentially in an alarmed state, as mentioned herein. The transmission may be executed via an RF or other signal, by implementing the transceiver located on the ST. Transmission-related different parameters such as: transmission encoding, protocol, rate and other parameters may be predefined for the CMS.

Data Reception from MU

Multiple STs may receive data from a single MU, such as but not limited to: type of information to transmit to MU (such as—full list of BT states, alarmed ST's only, alarmed of a certain kind only, or partial lists of such kind), time of next rendezvous, or other kinds of information.

In other embodiments more than one MU may be utilized to allow other farm handlers access to the information.

Mobile Unit

As shown in FIG. 2, ae mobile unit may only temporarily be present in the area of every feed lot (mobile by car or manually), and thus it is used for an occasional, predetermined and/or periodic data collection from the tags. The collected data is further transferred to the PC unit that may be located at the feed lot office, and used to process and store it for the system use.

Figure 8:
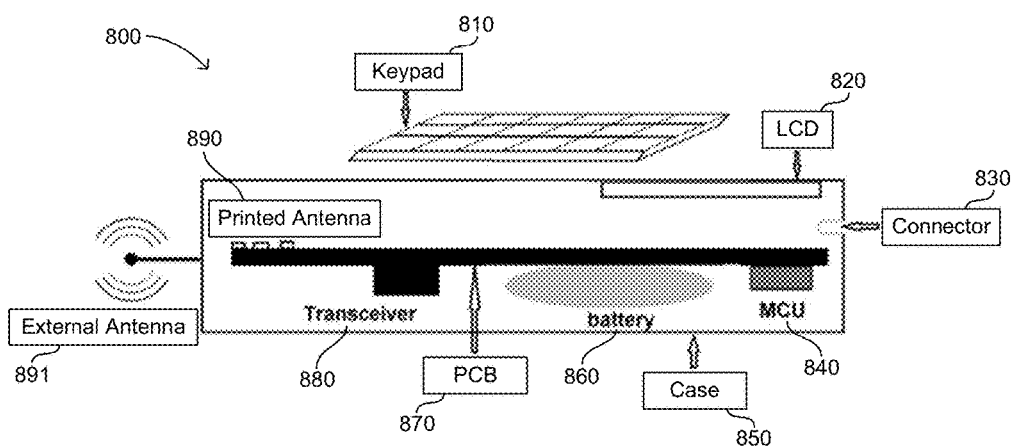
FIG. 8 shows a side view illustration of the inside of the mobile unit in FIG. 7.

A mobile unit or MU 800 may include one or more of the following components as shown in FIG. 8:
MCU 840
Transceiver 880
LCD (liquid crystal display) 820
Speaker (audio output)
Activation and control buttons on keypad 810
PCB printed circuit board 870
Case 850

Other components the MU may contain are optional components:
External memory
Rechargeable or disposable battery 860
Modem (cellular or other)
GPS
External antenna 891 and/or printed antenna 890
Connector 830

MU Structure

Figure 7:
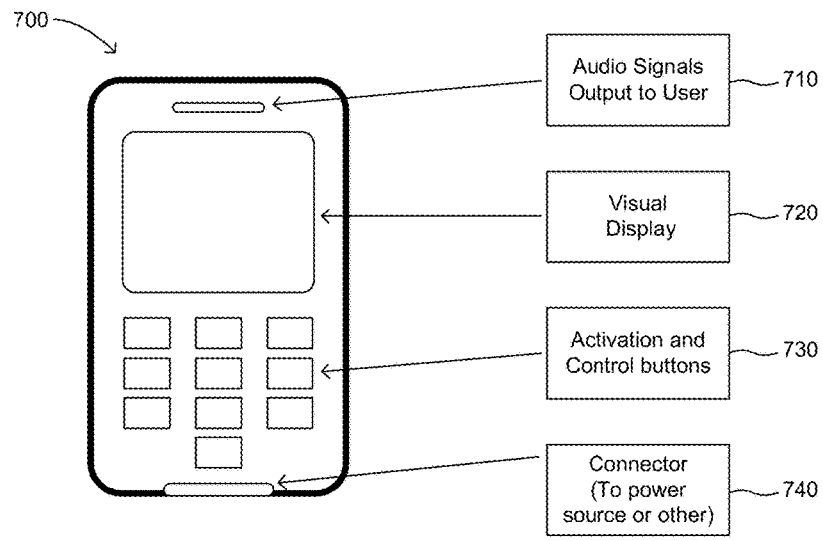
FIG. 7 shows an illustration of a mobile unit for use with the Basic and Smart tags in FIGS. 2-3.

Shown in FIG. 7 is mobile unit MU 700. MU 700 provides audio signals or output to users as shown in block 710.

Further MU 700 has a visual display 720 to allow end users to monitor the well-being and movement and other physical and physiological features of the livestock.

Activation and control button 730 allow the end user to control the MU 700. A connector 740 allows connection to a power source or other memory device or other device such as but not limited to a modem, GPS, computer, cellular phone, internet portal, charging station, or the like.

MU Functionality

The mobile unit allows a periodic collection of data stored in the STs. In order to collect the described data, the MU needs to be in a certain (predetermined) proximity to the cattle feed lot. The mobile unit is receiving instructions and tasks from the PC unit, by means of distal communication (RF) and/or manual communication (portable memory device). MU functionalities are:

Communication Functionality.

Communication with STS

Figure 9:
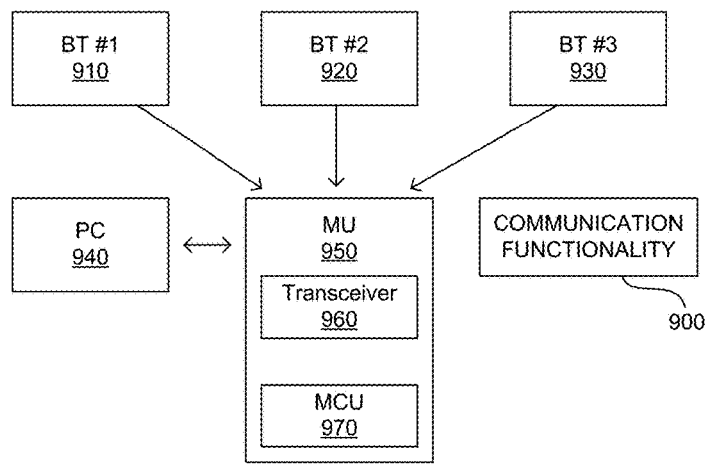
FIG. 9 shows a block diagram related to the mobile unit function for the unit in FIG. 7.

As shown in FIG. 9, the MU 950 receives a list of potentially alarmed BTs from the STs 910, 920, and 930, as described. The communication scheme 900 may be executed via an RF, by using the transceiver 960 located on the MU 950 or any other communication means depending on the embodiment. The communication with the STs may be done according to predetermined cycle or a rendezvous set with specific ST. Data is then stored on an external memory component such as PC 940 or MCU 970. ¶Relevant data to be sent to the STs is read from the MCU or external memory component, and sent to the STs via the transceiver. Transmission-related different parameters such as: transmission encoding, protocol, rate and other parameters may be predefined for the CMS.

Data Transmission and Communication with PC

Data received by the MU 950 is downloaded to the farm's PC 940 via the dedicated hardware (connector, such as but not limited to micro USB or USB). Optionally, data may be downloaded wirelessly in real time, by using a modem to transmit the information to the PC. Data is transferred from the MU memory to the relevant hardware via a pre-determined protocol.

In case of a wireless link between the MU and the PC unit, it also enables a dual way of communication between the PC and the MU units. The PC may send instructions or other information to the MU unit.¶¶

PC Unit

The PC serves as a main data collection, processing, saving and task management unit. Data gathered from mobile units is processed in order to extract information regarding potentially sick animals, animals that need to be extracted from herd or lot, and related information. An additional aspect related to the PC unit is tasks and instructions transfer to the MU. Such instructions may include, but are not limited to: routine/special stock management tasks, feeding and maintenance tasks, sick animal treatment, follow-up tasks etc. The PC unit may support more than one MU, enabling coverage of large area by MU's.

Figure 10:
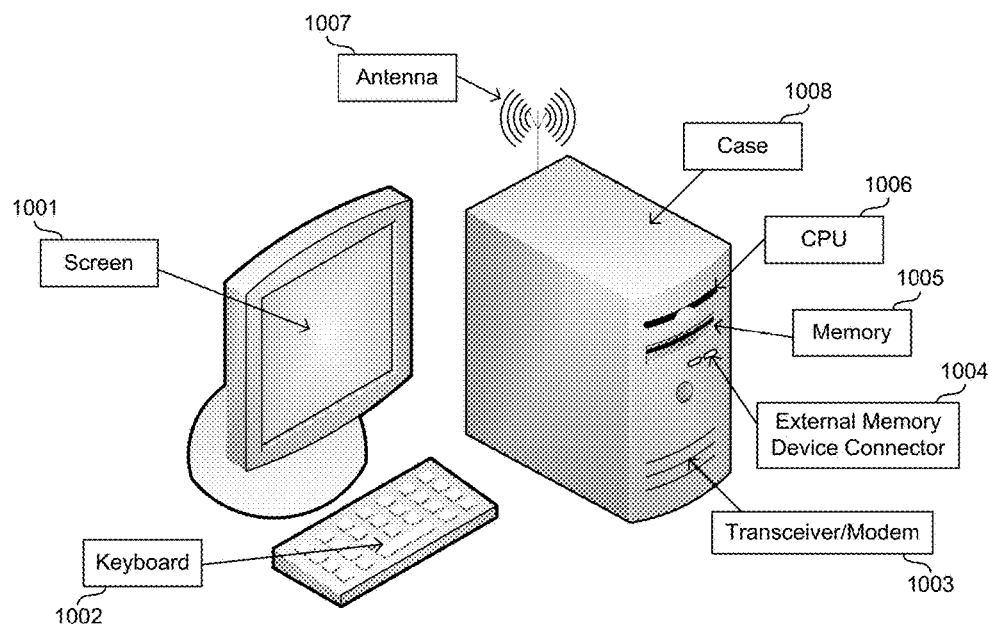
FIG. 10 shows an illustration of a stationary monitoring system for use with the Basic and Smart tags in FIGS. 2-3.

PC components include as shown in FIG. 10:
Screen 1001
Keyboard 1002
CPU (with suitable software) 1006
Memory 1005
Transceiver 1003 and antenna 1007
Optionally—connector for external memory device 1004
Case 1008

PC Structure

The PC (personal computer) is comprised from a screen and keyboard functioning as the user interface, and components that enable communication with the MU.

PC functionality includes for example, but is not limited to:
- Communication and data collection functionality
- Data processing and saving functionality
- Task management and instruction generation functionality Communication and Data Collection Functionality The PC receives data collected by the MU. Such data contains an updated list of all cattle IDs that transmitted being in alarm state during the last visit of the MU in the feed lot range. Data is received and collected from the MU via a dedicated hardware (such as portable memory device) or via a wireless connection (such as modem, cellular modem or possibly an RF communication.

Data Processing and Saving Functionality

Data received from the MU is processed on the PC's CPU, creating an updated report regarding the cattle in the whole farm feed lots area. Types of information and parameters the report may include: number of cattle extracted from feed lot due to high temperature or due to other reason, alarms due to low battery and other parameters.

In addition, the data may be processed in order to extract statistical information such as: differences in amount of cattle with high temperature between different locations in the feed lot grid, differences on time scale or as a result of changes implemented in the farm (for an example: comparing amount of cattle with high temperature in different seasons of year, after changing the sort of feed or feeding protocol, etc.) Processed data is then saved on the PC's memory.

Task Management and Instruction Generation Functionality

Information extracted from the processed data may be used in order to generate instructions for farm staff. General instructions (for an example—need to contact veterinarian, change feed type or alike) may be kept on the PC, while instructions regarding cattle located in the feed lot (for an example—recheck cattle with a particular ID number returned from veterinarian, change tags with low batteries) may be transmitted to the MU.

Possible Signs and Symptoms Monitoring, Using Different Kinds of Motion Sensor

For the purpose of this section and this entire description, a "motion sensor" means any kind of sensor that may provide information regarding the cattle's movement, locomotion, location and dislocation, such as an accelerometer, tilt sensor, magnetic sensor, piezo electric/piezo resistive sensor, proximity sensor in a form of a capacitive, inductive, magnetic, photoelectric, ultrasound, RF or other type of proximity sensor, also as a GPS sensor or other options.

Detection of Cattle Movement Speed.

The motion sensor detects any changes of the cattle dislocation and movement speed.

A slower moving herd or feed lot member may be suspected to be ill. Analysis of such sensor may include the average and the standard deviation of the animal's speed.

Detection of Movement Quantity.

The motion sensor detects each time the cattle moved during a pre-determined period of time. Hence sick cattle may not only moves slower, but also moves less times in general—such information may be valuable to monitor for illness.

The movement count may also include posture changes (such as if the cattle changed its posture from laying to standing, or from standing to walking). Analysis of such sensor may include the frequency of movements and time duration of each movement as well as the acceleration related to each movement.

Abnormal Movement Pattern Detection.

The information obtained from the motion sensor may be used for a pattern-recognition algorithm, monitoring changes in cattle behavior when compared to recorded history of the same cattle unit, or history of the whole herd or feed lot. Abnormal movement pattern may be movements in a different time of the day, to a different distance speed or acceleration, using a different route or different timing (for an example: if the cattle usually walks the whole distance to its feeding pan at one continuous walk, it may be suspected as ill or injured if it breaks the same route into several walking attempts or segments). Abnormal movement pattern may occur resulting from stiff movements, dragged knuckles or toes, weakness, fever or other signs or symptoms of illness.

Optionally, the abnormal pattern recognition may be executed in real-time, by comparing current behavior of a particular animal in the feed lot to the rest of the animals in the lot.

Trembling or Shivering Detection.

A motion sensor may be used to detect a cattle that is shivering—a possible result of high fever or weakness, characteristic to some illnesses.

Tail Movement Detection.

The pattern of the tail movements changes in various situations: when the animal feels threatened, alarmed, curious, on heat or sick. Cattle suspected to be ill are less prone to move its tail. Such a decrease in tail movements may be detected using a motion sensor.

Head Lowering Detection

A healthy cattle is expected to eat, and thus lower its head in a pattern suitable with the feeding process. Sick cattle, on the other hand, will sometimes keep its head in a pattern that might be different from its eating pattern. A motion sensor that may sample information about head lowering sequences and patterns in time, may contribute information about the animal's wellbeing.

Eating-Related Movement Detection.

a. One of the symptoms of illness in cattle may be the lack of or reduced appetite. Hence the feeding process in cattle causes some characteristic movements of the jaw, also as tilt of the head and neck—which are possible to measure using a motion sensor.

b. In addition, information about the feeding of the cattle may be obtained from the movements of the cattle's abdomen: when the guts are filled less than normal, the cow will appear slab-sided, and a slight shake of the abdomen may occur during walk.

c. Another possible way to monitor the cattle's feeding is through rumination monitoring. The amount of times the cattle is ruminating and/or the process duration might be different between healthy and ill cattle. Such a difference may be monitored using different kinds of motion sensor or other type of sensors—such as the ones monitoring for rumination sounds. The sensor should be attached proximally to the cattle's neck, reticulum, rumen or other location where rumination takes place.

Combination of Movement and Eating Pattern

An ill cattle may present a different behavior regarding its feeding patterns, such as: making less attempts to check for potential feed in different locations of the feeding lot, spending different amount of time next to the feeding pan or water tank, or spending different amount of time making non-feeding activities next to the feed pan (such as selfgrooming, social activity or other). Any change from a normal behavior pattern may be measured using a motion sensor.

Specifically, for the purpose of monitoring the proximity of cattle to its feeding pan, a particular implementation of magnetic and/or electromagnetic proximity sensor may be used; In order to access the feed in the pan, the cattle is inserting its head through the metal bars of the fence surrounding the feed lot.

Thus, a magnetic sensor located in the tag placed on the cattle may be used to sense the proximity to the metal and provide the CMS with information regarding feeding times and patterns. Alternatively, the proximity to the feeding pan may be monitored by using a short-range receiver placed on the pan, sensing the cattle tags from a pre-determined range.

Breathing Related Movement Detection.

An ill animal might suffer from breathing difficulties, expressed as labored breathing, increase in breathing rate and cough. A motion sensor measuring the relative movements of the animal's ribs or other location that is relevant to its respiratory system may provide with information regarding breathing deterioration.

Ear Movement and Position Detection

A possible sign of ill cattle is droopy ears. A motion sensor located on the cattle's ear and indicating the cattle's ear position regarding the ground, the cattle's head or other reference may provide with information about droopy ears and/or reduced ear movement.

Figure 11:
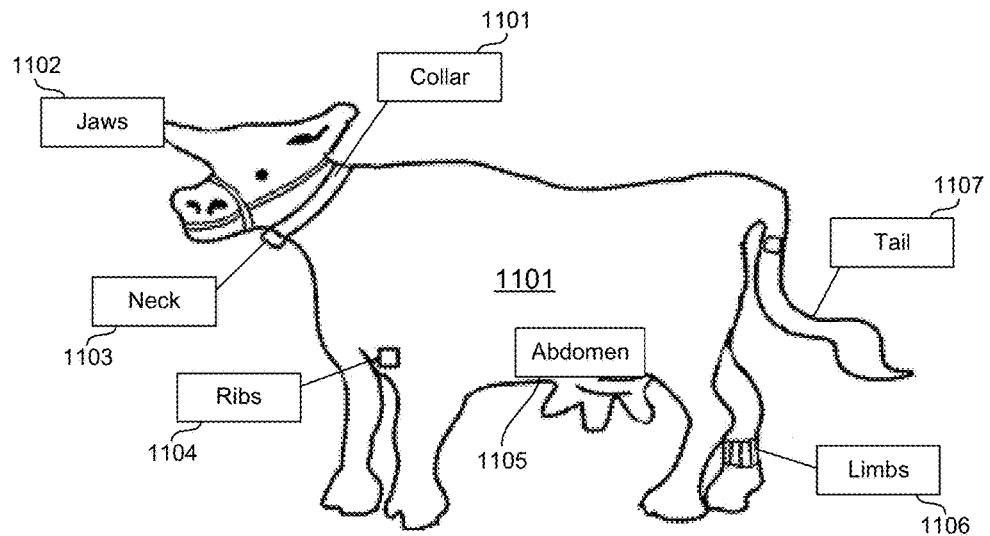
FIG. 11 shows an illustration of a livestock animal with potential tag sensor locations.

FIG. 11 illustrates the possible sensor location whether the sensor is a temperature sensor, or motion sensor or the like. Shown in FIG. 11 is a livestock animal in this case a cow or cattle 1100. Positions for the sensor or sensors may be placed by the gripper 395 previously shown and described at several locations. Some locations include, but are not limited to, collar 1101, jaws 1102, neck 1103, ribs 1104, and abdomen 1105 limb 1106 such as leg or legs and tail 1107.

Figure 12:
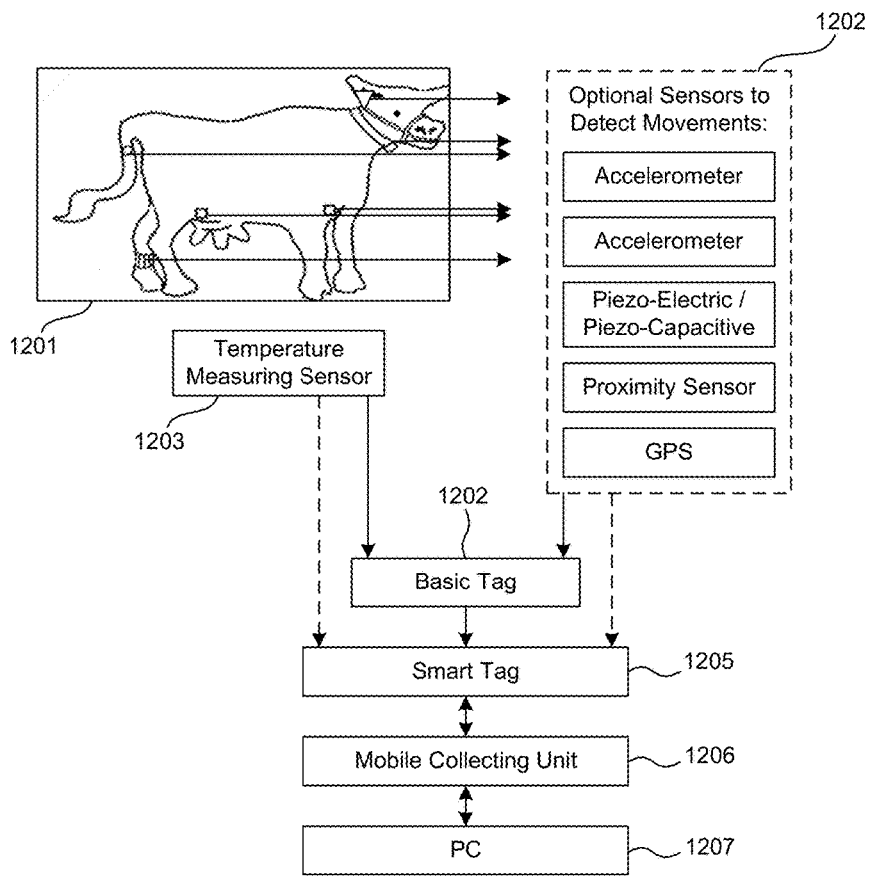
FIG. 12 shows a block diagram of data sampling and transmission for tag sensor locations.

FIG. 12 illustrates a block diagram of the livestock 1201 having sensors as shown in FIG. 11. Sensors may include for example optional sensors 1202 that include one or more of the following accelerometer, tilt switch, piezo electric/piezo capacitive, proximity sensor and/or GPS sensor. Information from these one or more sensors 1202 flow to BT 1204 and/or ST 1205 depending on the embodiment. Further BT 1204 relays information directly to ST 1205. Temperature measuring sensor 1203 also flows information to BT 1204 and optionally directly to ST 1205. ST 1205 communicates with the MU 1206 sending and receiving information to and from the MU 1206. MU 1206 sends instructions to the ST 1205. MU 1206 is connected to PC 1207 that also sends and receives information through the MU 1206 and gives instructions through MU 1206.

System Functionality Description Basic Tag

1. The data from all of the sensors located on the cattle is collected by the CPU and memory components on the BT. Data output to the ST is in form of: sampled raw data (such as voltage values sampled by the different sensors), or in the form of—; data processed into values (such as temperature and velocity values), or in the form of—threshold value (such as—normal or high temperature, normal or unexpected locomotion pattern), or in the form of—decision value: is the cow suspected to be ill or not.

2. The basic tag may transmit one or more of the following alarms regarding the cattle's wellbeing to the smart tag: about the cattle's temperature, eating or locomotion behavior.

3. Additional alarms transmitted by the basic tag may include: low battery, damaged tag or sensor.

4. The basic tag may transmit in case of a distress/error, or it may transmit data also if the cow is OK (no alarm requiring situation detected). Data output to ST includes also the cattle's ID.

Smart Tag

5. Data sampled from sensors may also be transmitted in its raw form from BT to ST. In such case, the raw data is processed in the ST in order to calculate measured values, threshold values or decision values (as described in previous descriptions of the basic tag functionality options).

6. The ST may use a database comprised of all tag ID's in a current lot, in order to allow a follow-up of the tags transmissions.

7. Optionally, only the last one or more transmissions of every basic tag will be saved in the ST. Alternatively, all the transmissions made to the ST in a pre-defined period of time (such as a day, two days, a week, etc.) may be saved in the ST dedicated component. For each transmission received there is an option to record the time of the transmission (in addition to tag's ID) which may be used for error analysis or alarm decisions.

8. No transmission from a basic tag during a period of 24 hours or other pre-determined period of time will be treated as an error: signal from basic tag is lost.

Figure 13:
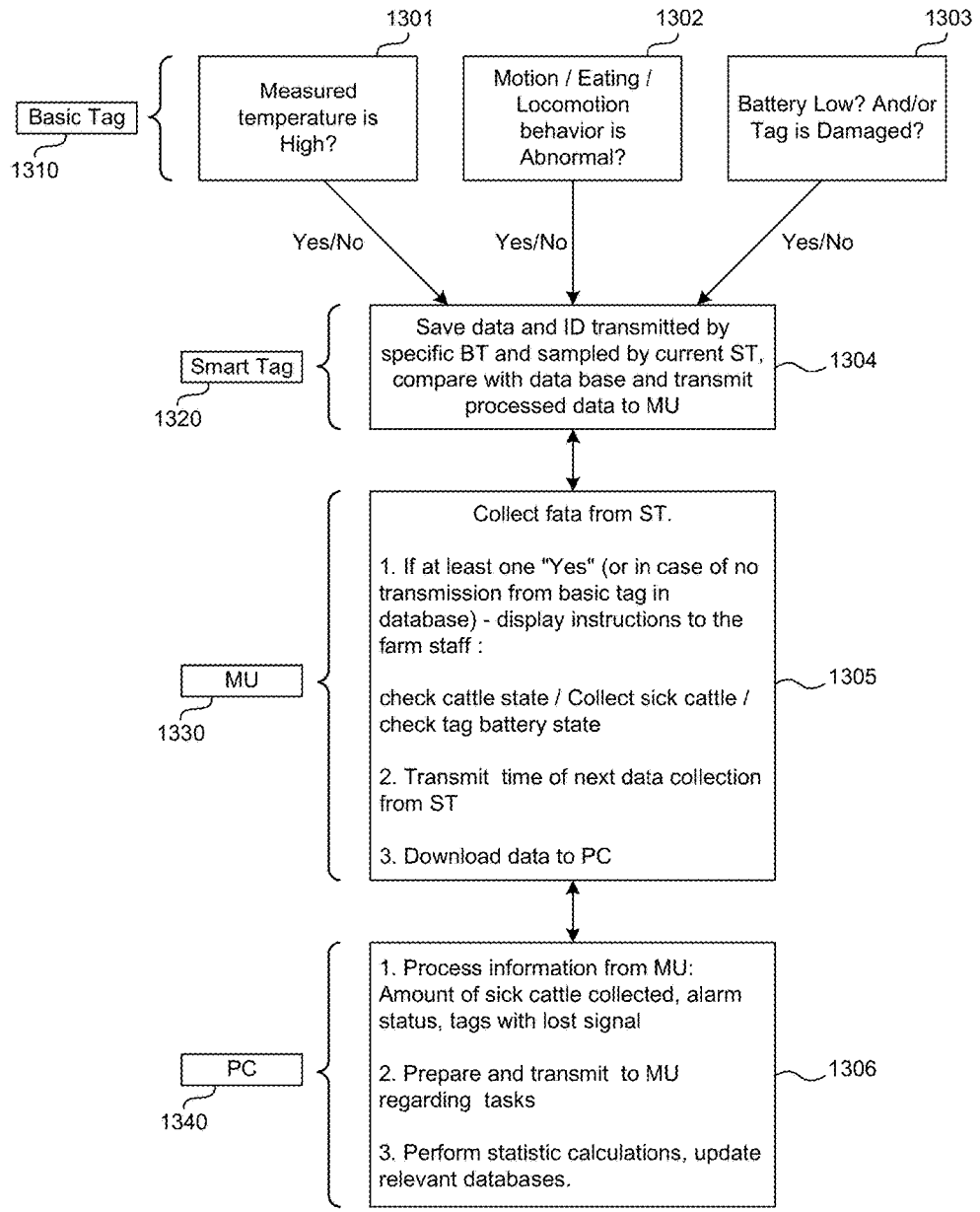
FIG. 13 shows a flow diagram for CMP system and/or CMS decision making process according to one embodiment.

In one embodiment, the decision making process of the CMP system may take the next form as shown in FIG. 13. Basic Tag 1310 identifies whether the animal temperature is high in block 1301. BT also determines motion, eating and other behavioral features in block 1302 BT also has the ability to identify whether the tag is damaged or the battery is low. All this information is communicated in this example to the Smart tag 1320.

In block 1304 the Smart tag saves data and has ID information transmitted by the specific BT and sampled by the current Smart tag (ST). The information is compared with a data base and information transmitted and process to a mobile unit (MU) 1330 in block 1305.

Depending on the embodiment, MU 1330 displays instructions to the farm staff and transmits time of next data collection as shown in block 1305. The information is also downloadable to a PC 1340. PC 1340 processes the information from the MU and prepares and transmits tasks to the MU. The PC 1340 also can perform statistical calculation and update all databases for further monitoring of the livestock.

Figure 14:
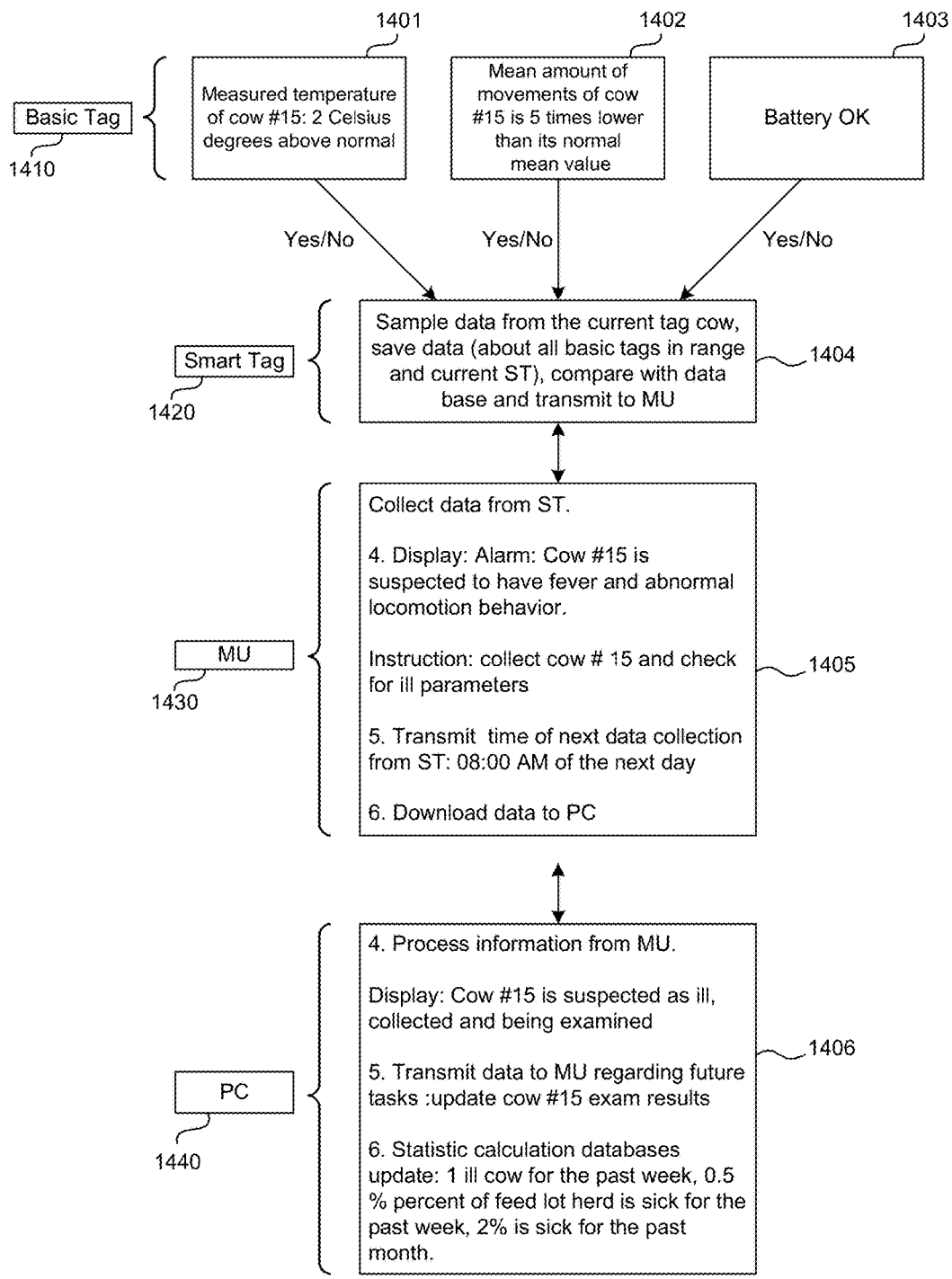
FIG. 14 shows a flow diagram for CMP system and/or CMS implementation for livestock with anomalous parameters.

FIG. 14 illustrates an example of CMS implementation in case of a cow with anomalous parameters. Basic tag 1410 measures a cow with above normal temperature in block 1401. In block 1402 the BT shows the mean amount of movements of the animal is significantly lower than its normal mean. In block 1403 the tag is reporting normal activity and function. All this information is transmitted to the ST 1420 in block 1404 where sample data from the current tagged cow is saved and compared with base data. This information is transmitted to MU 1430. The MU 1430 in block 1405 displays an Alarm for the cow and instructs the farm staff to collect the animal for observation and further testing. The information is downloaded to PC 1440 and time and date information is sent for the next data collection of the herd.

PC 1440 in block 1406 then processes the information from MU 1430 and displays that the cow is collected and being examined. Data is transmitted to the MU regarding future tasks and update on the collected cow. Statistical calculations may be performed on PC 1440 to update the percentage of ill animals per past week, month, year, and other statistical points of reference.

Figure 15:
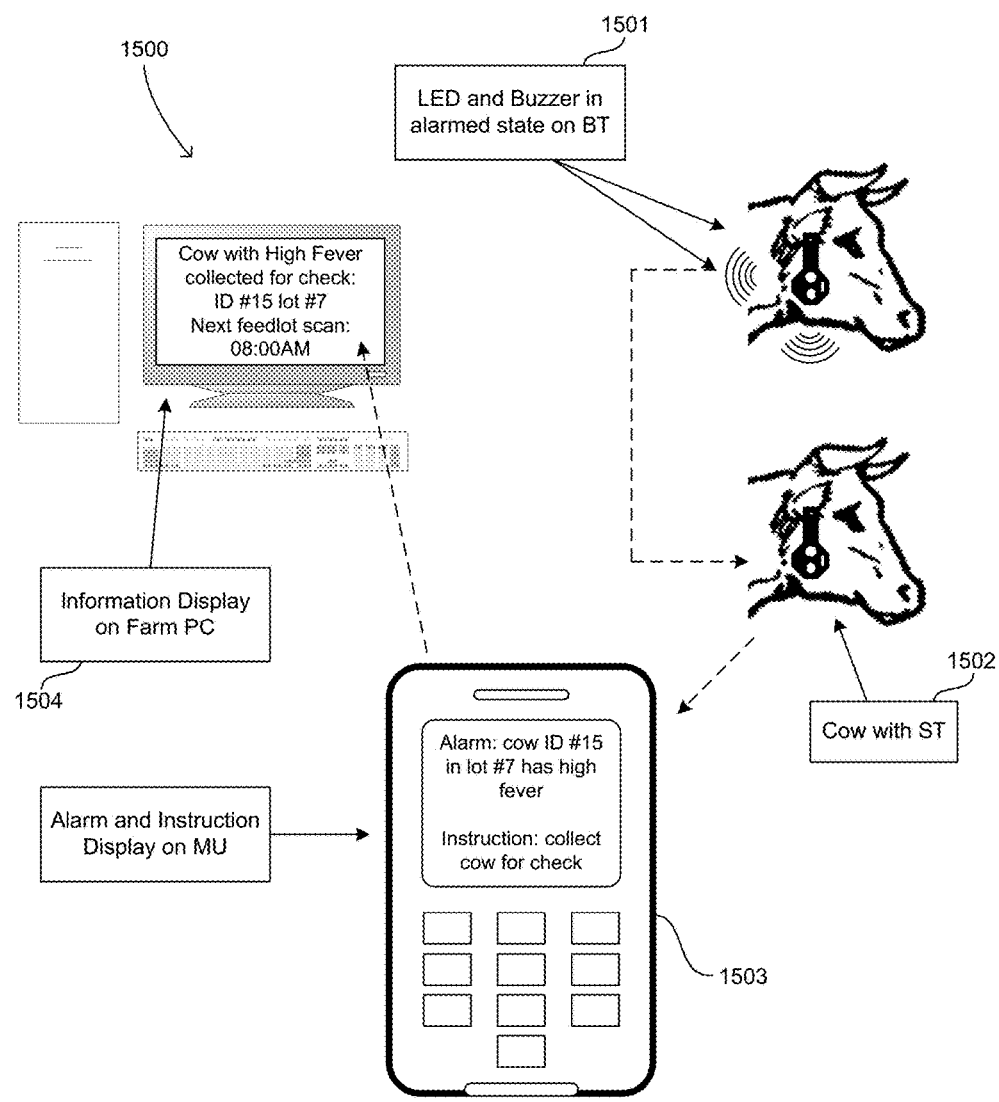
FIG. 15 shows an illustration of an example of CMS display for an alarm transmitting tag in FIG. 2-3.
Figure 16:
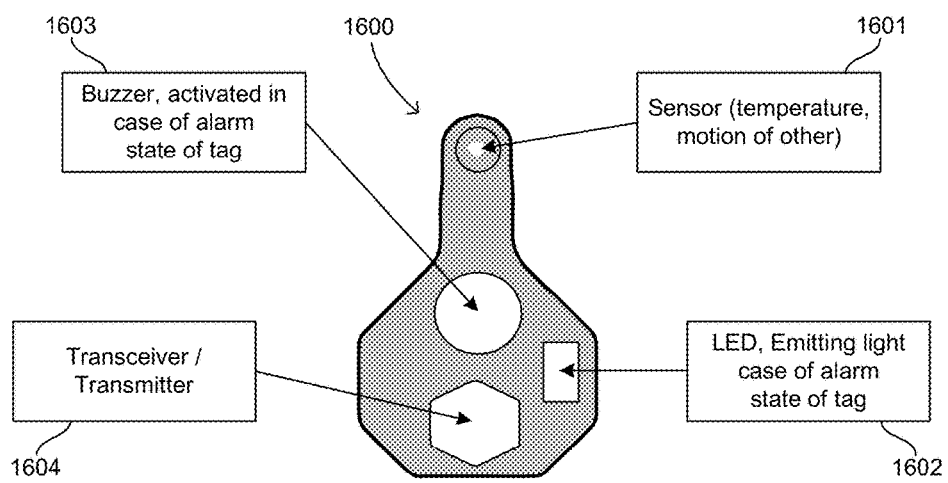
FIG. 16 shows an illustration of a tag for a Smart tag and/or Basic tag shown in FIG. 14.

FIG. 15 illustrates an alarm and instructions display on the MU. Shown is a CMS system 1500 having a MU 1503 and animals with BT 1501 and ST 1502. The ST 1502 transmits information to MU 1503 that the ST received from the BT 1501. Information is displayed on PC 1504 regarding the collection of the potentially ill animal FIG. 16 illustrates a legend of the ST and BT main components. Shown is tag 1600 having a sensor 1601 and LED 1602. The tag 1600 further contains a buzzer 1603 and a transmitter 1064. In the case of the ST the transmitter 1604 is a transceiver 1604 able to send and receive data, namely receive data from other BTs and/or STs and send the information to the MU and/or PC.

Figure 17:
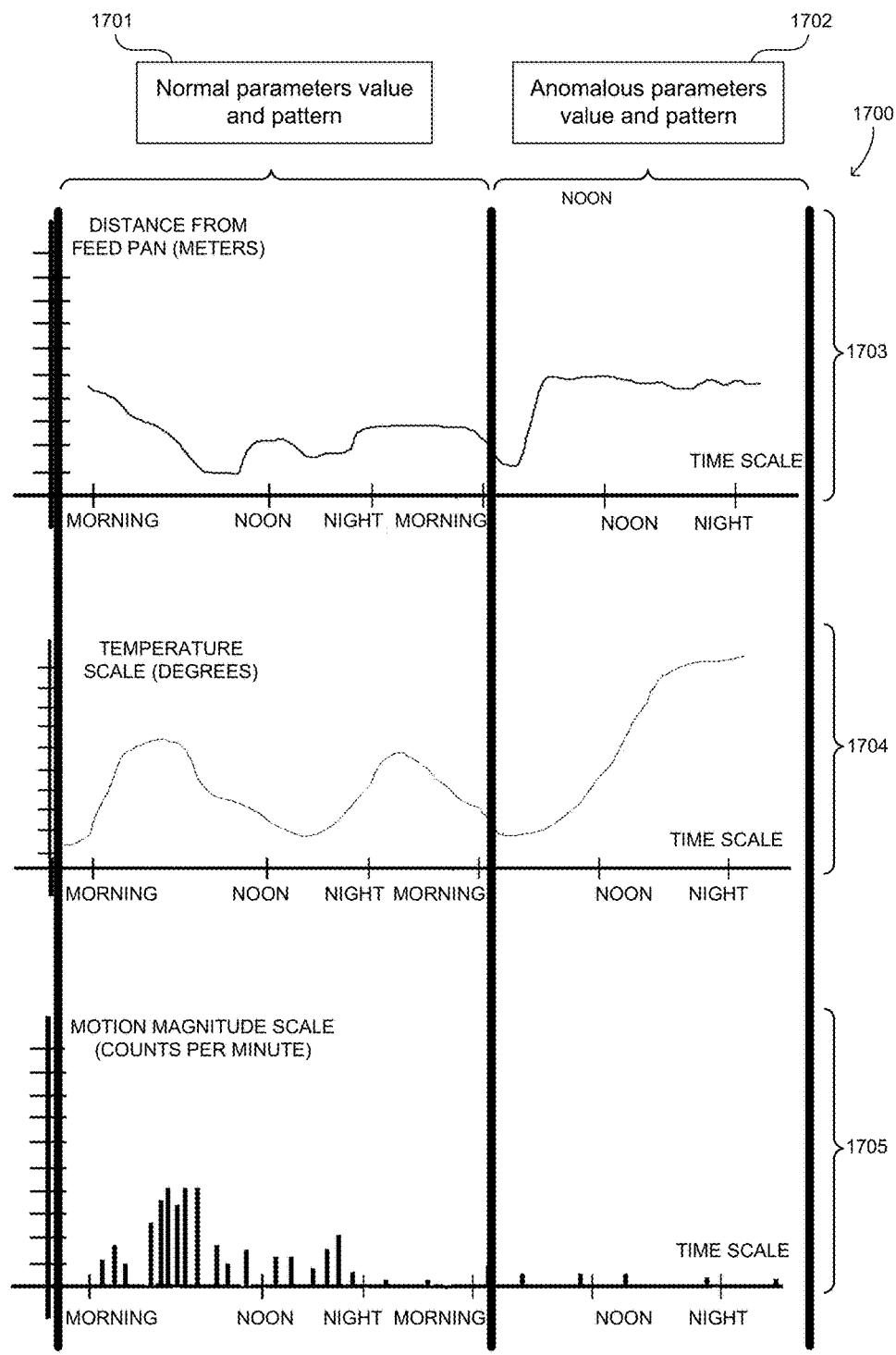
FIG. 17 shows a graphic depiction of an example of measured distance from feeding pan, motions quantity and temperature over a 48 hour period.

FIG. 17 demonstrates data sampling and processing by the CMS 1700: information regarding a single cattle unit motion and temperature is being gathered by the basic and smart tag. When processed and scaled over time, such information facilitates recognition of normal and anomalous parameter value and patterns. Shown are normal parameters value and pattern 1701 and anomalous parameters value and pattern 1702. Measured in this example is distance from feed pan 1703, temperature 1704 and magnitude of motion 1705. All this information is evaluated to identify the potential animal that carries an illness. The potentially ill animal is then detained and separated from the herd for further evaluation. Thereby, the risk of further exposure to a sick animal is minimized for the rest of the herd and cost savings are realized as well as healthier livestock due to this early detection.

Figure 18:
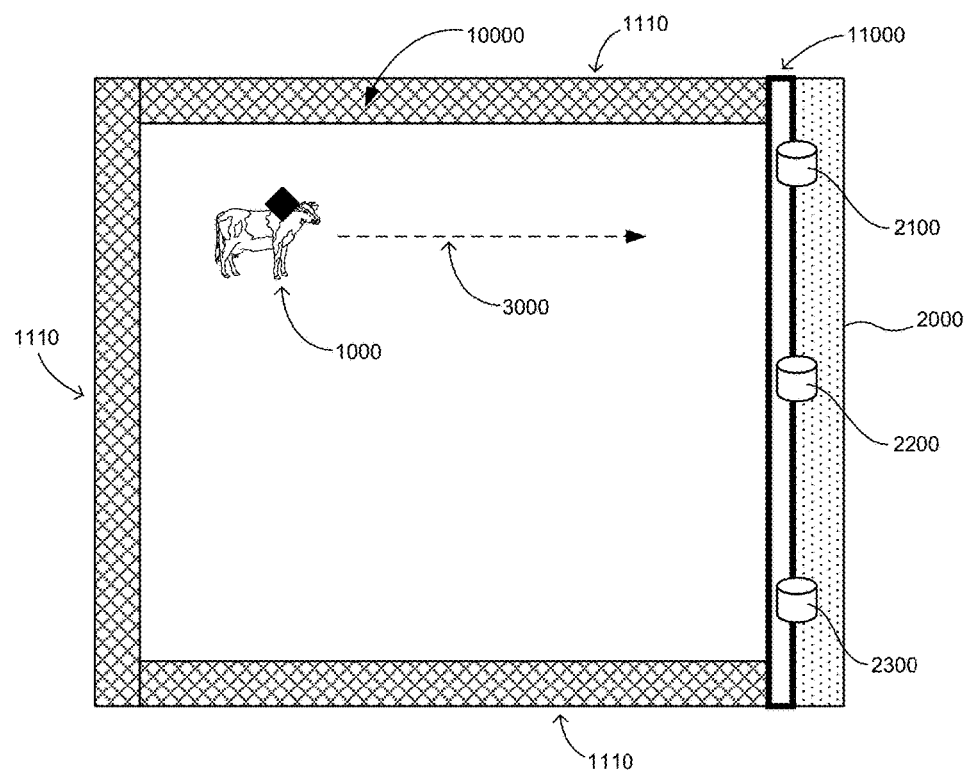
FIG. 18 shows an illustration of a livestock breading pen where the livestock has an attached tag.

FIG. 18 depicts a breading pen 10000. A livestock member 1000 having a tag attached to it, is typically moving in a general direction 3000 towards feeding area 2000. Approaching towards feeding area 2000, it will come in proximity to fence section 11000 that is part of the circumference fence 1110. A fence area 11000 is metal made, the magnetometer within the tag will provide indication that either (i) fence section 11000 is in proximity, or (ii) the livestock member 3000 is moving in a direction known as the feeding area 2000.

In an embodiment of the present invention, feeding area mounted units 2100, 2200, and 2300 comprise a transmitter component capable of transmitting information to a tag mounted on the livestock member 1000. Yet in an embodiment of the present invention, feeding area mounted units 2100, 2200, and 2300 comprise a receiver component capable of transmitting information to a tag mounted on the livestock member 1000. Such communication between the tag and the feeding area mounted units 2100, 2200, and 2300 may comprise information that will be transmitted or extracted for use by the herd operator.

Figure 19:
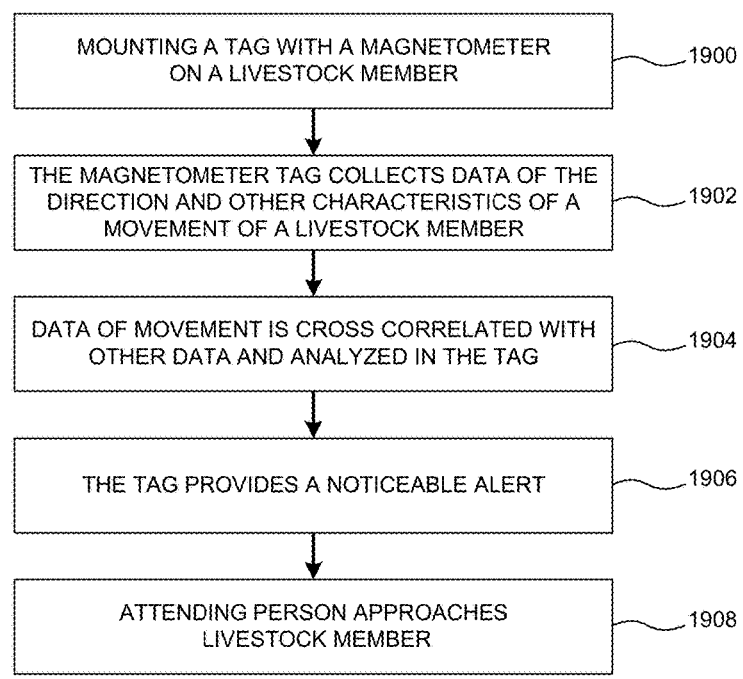
FIG. 19 shows an illustration of one process using a tag with a magnetometer component.

FIG. 19 depicts the process wherein the tag having a magnetometer component, is used to indicate a livestock member noticed as not moving about the pen as would be anticipated from a healthy eating livestock member. Block 1900 depicts mounting a tag with a magnetometer disposed on a livestock member. Next block 1902 depicts the magnetometer tag collecting data of the direction and other characteristics of a movement of a livestock member. Block 1904 illustrates data of movement of the livestock member is cross correlated with other data and analyzed in the tag. Block 1906 shows the tag provides a noticeable alert when a health condition or monitoring feature exceeds a predetermined level or exhibits unusual patterns based on past history of the livestock member. Block 1908 shows an attending person approaching the livestock member that has the alert activated. Again depending on the embodiment the noticeable alert may be visual, audible, electronic signaling or any combination thereof.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A veterinary monitoring system for monitoring livestock animals and early detection of animal illness, comprising:
　a plurality of tag units attached to the livestock animals for collecting data relating to one or more livestock behavioral patterns;
　each tag unit further having at least one transmitter and at least one receiver, and at least one contactless notable indication, and
　a bunk mounted unit attached to a livestock feeding bunk that is part of a livestock feeding pen, the bunk mounted unit having at least one receiver and at least one transmitter;
　wherein, the bunk unit is configured to receive the data from the tag units and transmit the data to the tag units;
　each tag unit is preprogrammed for time elapsed transmissions, whereby the tag units do not transmit data at the same time to overcome data loss due to tag data from multiple tag units being transmitted at the same time; and
　the tag unit provides indication radio frequency transmission independent of livestock location in the livestock feeding pen.

2. The system of claim 1 wherein each tag unit further includes a magnetometer that determines proximity to metal in the livestock feeding bunk.

3. The system of claim 1 wherein the at least one contactless notable indication is a visual indication.

4. The system of claim 1 wherein the at least one contactless notable indication is an acoustic indication.

5. The system of claim 4 wherein the acoustic indication is provided by a speaker.

6. The system of claim 3 wherein the visual indication is provided by a light source.

7. The system of claim 1 wherein the tag units transmit data using an acoustical signal.

8. The system of claim 1 wherein the tag units transmit data using a light signal.

9. The system of claim 1, wherein each tag further includes a sensor configured to collect data characterizing a movement of the livestock member, and wherein each tag is configured to:
　analyze the collected data; and
　provide a radio frequency data transmission when the data indicates a health condition of the livestock member.

10. A method for identifying an ill livestock member of a group of livestock, comprising the steps of:
　mounting a tag onto a livestock member of the group of livestock;
　actuating a notable indication within the tag, and the tag is preprogrammed for time elapsed transmissions whereby the tag does not transmit data at the same time as another tag mounted to the same or different member of the group of livestock to overcome data loss due to data from multiple tags being transmitted at the same time, and the tag provides radio frequency transmission independent of livestock location;

receiving the radio frequency transmission with a bunk mounted unit attached to a livestock feeding bunk;

relaying the radio frequency transmission from a bunk mounted unit to a mobile unit;

using the mobile device for identifying the tag; and wherein the mobile device identifies the notable indication of the tag.

11. The method disclosed in claim 10, wherein the notable indication is a light signal, and the mobile device includes a polarized lens to provide for outstanding of the light signal.

12. The method disclosed in claim 10, wherein the notable indication is an acoustical signal, and the mobile device includes a microphone for identifying the acoustical signal.

13. A method of identifying an ill livestock member, comprising the steps of:

obtaining a plurality of livestock tags, each tag includes a sensor selected from the group consisting of a temperature sensor movement sensor, acceleration sensor, light sensor, sound sensor, a magnetometer, and any combination thereof; said sensor enclosed in the tag that is attached to the livestock;

obtaining a bunk mounted unit attached to a livestock feeding bunk that is part of a livestock feeding pen, the bunk mounted unit having at least one receiver and at least one transmitter, the bunk mounted unit includes at least one of: an acoustic transmitter component; a speaker; an acoustic receiver component; a microphone; a light emitting diode (LED), and a photo diode; wherein said receiver and transmitter components are used for data exchange with the livestock tags;

actuating a notable indication within at least one tag, and the tag is preprogrammed for time elapsed transmissions whereby the tag does not transmit data at the same time as another one of the tags to overcome data loss due to data from multiple tags being transmitted at the same time, and the tag provides a radio frequency transmission independent of livestock location;

receiving the radio frequency transmission with the bunk mounted unit attached to a livestock feeding bunk;

relaying the radio frequency transmission from a bunk mounted unit to a mobile unit;

logging data selected from a group consisting of the tags, the bunk mounted unit, the mobile unit, and any combination thereof; and forwarding said data from the mobile device to a stationary site.

14. The method disclosed in claim 13, wherein each tag further includes a component selected from a group consisting of an acoustic transmitter component, a speaker, an acoustic receiver component, a microphone, a light emitting diode (LED), wherein the at least one LED emits light of a different wave lengths, a photo diode ("light sensor"), and any combination thereof; and wherein each tag also comprises a radio transceiver component selected from a group consisting of RF, Wi-Fi, Bluetooth, and any combination thereof for transmitting data and wherein the tag further includes an antenna.

15. The method of claim 10, further comprising, applying to a livestock animal a tag having a magnetometer with a component selected from a group consisting of an axial component, an accelerometer, and any combination thereof with at least one axial measurement capability for identifying head position and movement, habits location, state of health and any combination thereof of the livestock animal; and wherein, the magnetometer actuates the tag when the tag is in a proximity of metal.

16. A device for identifying livestock, comprising a tag comprising a magnetometer, wherein the tag is placed on a livestock animal to identify, track and record information indicative of head movements and location of the livestock animal's proximity to a livestock feeding bunk in a livestock feeding pen;

the tag having a transmitter to transmit information and a receiver to receive information from another device;

the tag further including an alert system to identify a certain livestock animal among a herd of livestock animals and alert farmers for improved health management of the livestock animal;

wherein, the tag unit is preprogrammed for time elapsed transmissions whereby the tag does not transmit data at the same time as other tags mounted to the livestock to overcome data loss due to data from the other livestock tags being transmitted at the same time; and the tag unit provides an indication independent of livestock location in the livestock feeding pen.

17. The device of claim 16 wherein the tag further includes a gripper for attaching to the livestock animal.

18. The device of claim 17 wherein the tag is attached in an ear area of the livestock animal.

19. The device of claim 16 wherein the tag includes a surface temperature sensor.

20. The device of claim 16 wherein the tag includes an ear surface temperature sensor.

21. The device of claim 16 wherein the alert system includes an alarm selected from the group consisting of an audible alert, a visual alert, an electronic alert and any combination thereof.

* * * * *

UNITED STATES PATENT AND TRADEMARK OFFICE
CERTIFICATE OF CORRECTION

PATENT NO. : 10,045,511 B1
APPLICATION NO. : 15/232239
DATED : August 14, 2018
INVENTOR(S) : Moshe Yarden et al.

It is certified that error appears in the above-identified patent and that said Letters Patent is hereby corrected as shown below:

In the Claims

Column 23, Line 7, delete "unit" in both places and add --device-- in its place.
Column 23, Line 24, after "livestock" add --member--.
Column 23, Line 44, after "mobile" delete "unit" and add --device-- in its place.
Column 23, Line 46, after "mobile" delete "unit" and add --device-- in its place.

Signed and Sealed this
Thirtieth Day of April, 2019

Andrei Iancu
*Director of the United States Patent and Trademark Office*